US008569379B2

(12) United States Patent
Petit et al.

(10) Patent No.: US 8,569,379 B2
(45) Date of Patent: Oct. 29, 2013

(54) USE OF RASAGILINE FOR THE TREATMENT OF OLFACTORY DYSFUNCTION

(75) Inventors: Geraldine Petit, Lund (SE); Patrik Brundin, Lund (SE)

(73) Assignee: Teva Pharmaceutical Industries Ltd., Petach-Tikva (IL)

(*) Notice: Subject to any disclaimer, the term of this patent is extended or adjusted under 35 U.S.C. 154(b) by 213 days.

(21) Appl. No.: 13/192,019

(22) Filed: Jul. 27, 2011

(65) Prior Publication Data
US 2012/0029087 A1 Feb. 2, 2012

Related U.S. Application Data

(60) Provisional application No. 61/437,212, filed on Jan. 28, 2011, provisional application No. 61/400,464, filed on Jul. 27, 2010.

(51) Int. Cl.
A01N 33/02 (2006.01)
A61K 31/135 (2006.01)

(52) U.S. Cl.
USPC .......................................................... 514/657

(58) Field of Classification Search
USPC .......................................................... 514/657
See application file for complete search history.

(56) References Cited

U.S. PATENT DOCUMENTS

| | | | |
|---|---|---|---|
| 5,387,612 A | 2/1995 | Youdim et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,668,181 A | 9/1997 | Youdim et al. |
| 5,744,500 A | 4/1998 | Youdim et al. |
| 5,786,390 A | 7/1998 | Youdim et al. |
| 5,891,923 A | 4/1999 | Youdim et al. |
| 6,126,968 A | 10/2000 | Peskin et al. |
| 6,277,886 B1 | 8/2001 | Levy et al. |
| 6,316,504 B1 | 11/2001 | Youdim et al. |
| 6,462,222 B1 | 10/2002 | Chorev et al. |
| 6,630,514 B2 | 10/2003 | Youdim et al. |
| 6,956,060 B2 | 10/2005 | Youdim et al. |
| 7,396,860 B2 | 7/2008 | Blaugrund et al. |
| 7,491,847 B2 | 2/2009 | Frenkel |
| 7,547,806 B2 | 6/2009 | Frenkel et al. |
| 7,572,834 B1 | 8/2009 | Sterling et al. |
| 7,598,420 B1 | 10/2009 | Sterling et al. |
| 7,619,117 B1 | 11/2009 | Lidor-Hadas et al. |
| 7,750,051 B2 | 7/2010 | Frenkel et al. |
| 7,815,942 B2 | 10/2010 | Peskin |
| 7,855,233 B2 | 12/2010 | Frenkel et al. |
| 7,968,749 B2 | 6/2011 | Frenkel et al. |
| 8,080,584 B2 | 12/2011 | Safadi et al. |
| 8,143,315 B2 | 3/2012 | Stahl et al. |
| 8,334,409 B2 | 12/2012 | Frenkel |
| 2004/0127577 A1 | 7/2004 | Blaugrund et al. |
| 2006/0018957 A1 | 1/2006 | Lerner et al. |
| 2006/0094783 A1 | 5/2006 | Youdim |
| 2007/0100001 A1 | 5/2007 | Youdim |
| 2007/0232700 A1 | 10/2007 | Blaugrund et al. |
| 2009/0036411 A1 | 2/2009 | Henry et al. |
| 2009/0062400 A1 | 3/2009 | Oron et al. |
| 2009/0076160 A1 | 3/2009 | Lendvai et al. |
| 2009/0111892 A1 | 4/2009 | Patashnik et al. |
| 2009/0181086 A1 | 7/2009 | Safadi et al. |
| 2009/0312436 A1 | 12/2009 | Levy et al. |
| 2010/0008983 A1 | 1/2010 | Safadi et al. |
| 2010/0010095 A1 | 1/2010 | Frenkel |
| 2010/0137447 A1 | 6/2010 | Lehmann et al. |
| 2010/0144887 A1 | 6/2010 | Frenkel et al. |
| 2010/0145101 A1 | 6/2010 | Frenkel et al. |
| 2010/0168239 A1 | 7/2010 | Poewe |
| 2010/0189788 A1 | 7/2010 | Safadi et al. |
| 2010/0189790 A1 | 7/2010 | Safadi et al. |
| 2010/0189791 A1 | 7/2010 | Safadi et al. |
| 2010/0234636 A1 | 9/2010 | Stahl |
| 2011/0130466 A1 | 6/2011 | Lorenzl |
| 2011/0152381 A1 | 6/2011 | Frenkel et al. |
| 2011/0313050 A1 | 12/2011 | Rimkus et al. |
| 2012/0003310 A1 | 1/2012 | Safadi et al. |
| 2012/0059058 A1 | 3/2012 | Lorimer et al. |
| 2012/0100189 A1 | 4/2012 | Safadi et al. |
| 2012/0101168 A1 | 4/2012 | Bahar et al. |
| 2012/0238636 A1 | 9/2012 | Patashnik et al. |
| 2012/0263789 A1 | 10/2012 | Safadi et al. |

FOREIGN PATENT DOCUMENTS

| | | |
|---|---|---|
| WO | WO 2009/003147 | 12/2008 |
| WO | WO 2010/070090 | 6/2010 |
| WO | WO 2011/003938 | 1/2011 |

OTHER PUBLICATIONS

PCT International Preliminary Report on Patentability, issued Jan. 29, 2013 in connection with PCT/US2011/045574, filed Jul. 27, 2011.
U.S. Appl. No. 13/859,625, filed Apr. 9, 2013, Levy et al.
U.S. Appl. No. 12/283,107, filed Sep. 8, 2008, Sterling et al.
U.S. Appl. No. 13/647,658, filed Oct. 9, 2012, Ulanenko et al.
U.S. Appl. No. 13/647,685, filed Oct. 9, 2012, Safadi et al.
U.S. Appl. No. 13/647,622, filed Oct. 9, 2012, Safadi et al.
U.S. Appl. No. 13/651,307, filed Oct. 12, 2012, Levy et al.
International Search Report and Written Opinion of the International Searching Authority for International Application No. PCT/US2011/045574, issued Dec. 8, 2011.
Bohnen et al., "Olfactory dysfunction, central cholinergic integrity and cognitive impairment in Parkinson's disease," Brain, 2010, 133(6):1747-1754.
Chen et al., "Conditional ablation of mature olfactory sensory neurons mediated by diphtheria toxin receptor," Journal of Neurocytology, 2005 34:37-47.
Evans et al., "Olfactory dysfunction: testing in neurological disorders," 1988, http://journals.lww.com/co-neurology/Citation/1988/01050/Olfactory_dysfunction_testing_in_neurological.21.aspx.
Fleming et al., "Olfactory deficits in mice overexpressing human wildtype alpha-synuclein", Eur. J. Neurosci., Jul. 28, 2008(2): 247-56.

(Continued)

Primary Examiner — Marcos Sznaidman
(74) Attorney, Agent, or Firm — John P. White; Gary J. Gershik; Cooper & Dunham LLP

(57) ABSTRACT

Disclosed are methods of treating olfactory dysfunction by periodically administering a therapeutically effective amount of rasagiline or a pharmaceutically acceptable salt of rasagiline to a subject.

13 Claims, 7 Drawing Sheets

(56) References Cited

OTHER PUBLICATIONS

Grand Rounds Presentation, UTMB, Dept. of Otolaryngology, "Olfactory Dysfunction and Disorders", retrieved Nov. 9, 2012, <www.utmb.edu/otoref/grnds/Olfactory-2003-1126/Olfactory-2003-1126.htm>.

Herting, et al., "Olfactory dysfunction in Parkinson's disease: its role as a new cardinal sign in early and differential diagnosis," Nervenarzt, 2008, 79(2):175-84 (Abstract Only).

Lane et al., "Development of transgenic mouse models for the study of human olfactory dysfunction," Am J Rhinol., 2005, 19(3):229-35 (Abstract Only).

Lane et al., "A genetic model of chronic rhinosinusitis-associated olfactory inflammation reveals reversible functional impairment and dramatic neuroepithelial reorganization," The Journal of Neuroscience, 2010, 30(6):2324-2329.

"New findings reveal loss of smell function may predict early onset of Alzheimer's disease," News U Can Use, accessed Jul. 26, 2010, www.newsucanuse.org/node/351.

Reichmann, "Olfactory dysfunction in early pd suggests that the disease is caused by a toxin," http://www.comtecmed.com/CONY/Uploads/assets/abstracts/reichmann.pdf, accessed Jan. 10, 2013.

Turner et al., "Reversible loss of neuronal marker protein expression in a transgenic mouse model for sinusitis-associated olfactory dysfunction," Am J Rhinol Allergy, 2005, 24(3)192-6 (Abstract Only).

Wetzel et al., "Cellular Mechanisms of Olfactory Signal Transduction," Chem. Senses, 2005, 30(supp 1):1321-1322.

A.

B.

C.

A.

B.

C.

A.

B.

C.

A.

B.

A.

B.

A.

B.

A.

B.

USE OF RASAGILINE FOR THE TREATMENT OF OLFACTORY DYSFUNCTION

This application claims benefit of U.S. Provisional Application Nos. 61/437,212, filed Jan. 28, 2011 and 61/400,464, filed Jul. 27, 2010, the contents of each of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Olfactory dysfunction can arise from a variety of causes and can profoundly influence a patient's quality of life. Studies have shown that olfactory dysfunction affects at least 1% of the population under the age of 65 years, and well over 50% of the population older than 65 years. The sense of smell contributes to the flavor of foods and beverages and also serves as an early warning system for the detection of environmental hazards, such as spoiled food, leaking natural gas, smoke, or airborne pollutants. The losses or distortions of smell sensation can adversely influence food preference, food intake and appetite (1), which in turn will adversely affect the health of patients.

Three specialized neural systems are present within the nasal cavities in humans. They are 1) the main olfactory system (cranial nerve I), 2) trigeminal somatosensory system (cranial nerve V), 3) the nervus terminalis (cranial nerve 0). CN I mediates odor sensation. It is responsible for determining flavors. CN V mediates somatosensory sensations, including burning, cooling, irritation, and tickling. CN 0 is a ganglionated neural plexus. It spans much of the nasal mucosa before coursing through the cribriform plate to enter the forebrain medial to the olfactory tract. The exact function of the nervus terminalis is unknown in humans (1).

The olfactory neuroepithelium is a pseudostratified columnar epithelium. The specialized olfactory epithelial cells are the only group of neurons capable of regeneration. The olfactory epithelium is situated in the superior aspect of each nostril, including cribriform plate, superior turbinate, superior septum, and sections of the middle turbinate. It harbors sensory receptors of the main olfactory system and some CN V free nerve endings. The olfactory epithelium loses its general homogeneity postnatally, and as early as the first few weeks of life metaplastic islands of respiratory-like epithelium appear. The metaplasia increases in extent throughout life. It is presumed that this process is the result of insults from the environment, such as viruses, bacteria, and toxins (1).

There are 6 distinct cells types in the olfactory neuroepithelium: 1) bipolar sensory receptor neurons, 2) microvillar cells, 3) supporting cells, 4) globose basal cells, 5) horizontal basal cells, 6) cells lining the Bowman's glands. There are approximately 6,000,000 bipolar neurons in the adult olfactory neuroepithelium. They are thin dendritic cells with rods containing cilia at one end and long central processes at the other end forming olfactory fila. The olfactory receptors are located on the ciliated dendritic ends. The unmyelinated axons coalesce into 40 bundles, termed olfactory fila, which are ensheathed by Schwann-like cells. The fila transverses the cribriform plate to enter the anterior cranial fossa and constitute CN I. Microvillar cells are near the surface of the neuroepithelium, but the exact functions of these cells are unknown. Supporting cells are also at the surface of the epithelium. They join tightly with neurons and microvillar cells. They also project microvilli into the mucus. Their functions include insulating receptor cells from one another, regulating the composition of the mucus, deactivating odorants, and protecting the epithelium from foreign agents. The basal cells are located near the basement membrane, and are the progenitor cells from which the other cell types arise. The Bowman's glands are a major source of mucus within the region of the olfactory epithelium (1).

The odorant receptors are located on the cilia of the receptor cells. Each receptor cell expresses a single odorant receptor gene. There are approximately 1,000 classes of receptors at present. The olfactory receptors are linked to the stimulatory guanine nucleotide binding protein Golf. When stimulated, it can activate adenylate cyclase to produce the second messenger cAMP, and subsequent events lead to depolarization of the cell membrane and signal propagation. Although each receptor cell only expresses one type of receptor, each cell is electrophysiologically responsive to a wide but circumscribed range of stimuli. This implies that a single receptor accepts a range of molecular entities (1).

The olfactory bulb is located on top of the cribriform plate at the base of the frontal lobe in the anterior cranial fossa. It receives thousands of primary axons from olfactory receptor neurons. Within the olfactory bulb, these axons synapse with a much smaller number of second order neurons which form the olfactory tract and project to olfactory cortex. The olfactory cortex includes the frontal and temporal lobes, thalamus, and hypothalamus (1).

Olfactory disorders can be classified as follows: 1) anosmia: inability to detect qualitative olfactory sensations (i.e., absence of smell function), 2) partial anosmia: ability to perceive some, but not all, odorants, 3) hyposmia or microsmia: decreased sensitivity to odorants, 4) hyperosmia: abnormally acute smell function, 5) dysosmia (cacosmia or parosmia): distorted or perverted smell perception or odorant stimulation, 6) phantosmia: dysosmic sensation perceived in the absence of an odor stimulus (a.k.a. olfactory hallucination), 7) olfactory agnosia: inability to recognize an odor sensation (1).

It is also useful to classify olfactory dysfunction into three general classes: 1) conductive or transport impairments from obstruction of nasal passages (e.g. chronic nasal inflammation, polyposis, etc.), 2) sensorineural impairments from damage to neuroepithelium (e.g. viral infection, airborne toxins, etc.), 3) central olfactory neural impairment from central nervous system damage (e.g. tumors, masses impacting on olfactory tract, neurodegenerative disorders, etc.). These categories are not mutually exclusive. For example: viruses can cause damage to the olfactory neuroepithelium and they may also be transported into the central nervous system via the olfactory nerve causing damage to the central elements of the olfactory system (1).

The etiology of most cases of olfactory dysfunction can be ascertained from carefully questioning the patient about the nature, timing, onset, duration, and pattern of their symptoms. It is important to determine the degree of olfactory ability prior to the loss. And any historical determination of antecedent events, such as head trauma, upper respiratory infection, or toxic exposure, should be sought. Fluctuations in function and transient improvement with topical vasoconstriction usually indicate obstructive, rather then neural, causes. Medical conditions frequently associated with olfactory dysfunction should be identified, such as epilepsy, multiple sclerosis, Parkinson's disease, and Alzheimer's disease. Also any history of sinonasal disease and allergic symptoms, including any previous surgical therapy for sinonasal disease should be investigated. In addition, patients who complain of taste loss, upon quantitative olfactory testing usually reveal an olfactory disorder (1).

Disclosed herein is that rasagiline effectively treats olfactory dysfunction. Rasagiline, R(+)-N-propargyl-1-aminoindan, is a potent second generation monoamine oxidase (MAO) B inhibitor (Finberg et al., Pharmacological properties of the anti-Parkinson drug rasagiline; modification of endogenous brain amines, reserpine reversal, serotonergic and dopaminergic behaviours, Neuropharmacology (2002) 43(7):1110-8). Rasagiline Mesylate in a 1 mg tablet is commercially available for the treatment of idiopathic Parkinson's disease as Azilect® from Teva Pharmaceuticals Industries, Ltd. (Petach Tikva, Israel) and H. Lundbeck A/S (Copenhagen, Denmark).

SUMMARY OF THE INVENTION

The subject invention provides a method of treating a symptom of olfactory dysfunction in a subject afflicted by olfactory dysfunction, the method comprising:
a) identifying the subject as afflicted by olfactory dysfunction, and
b) periodically administering to the subject so identified an amount of R(+)-N-propargyl-1-aminoindan or a pharmaceutically acceptable salt thereof, effective to treat the subject.

The subject invention also provides a method of reducing the rate of progression of olfactory dysfunction in a non-Parkinson's disease subject afflicted by olfactory dysfunction, the method comprising periodically administering to the subject an amount of R(+)-N-propargyl-1-aminoindan or a pharmaceutically acceptable salt thereof effective to reduce the rate of progression of olfactory dysfunction in the non-Parkinson's disease subject.

The subject invention further provides a method of inhibiting loss of olfactory function in a non-Parkinson's disease subject, the method comprising periodically administering to the subject an amount of R(+)-N-propargyl-1-aminoindan or a pharmaceutically acceptable salt thereof effective to inhibit loss of olfactory function in the non-Parkinson's disease subject.

DETAILED DESCRIPTION OF THE INVENTION

Figure 1:
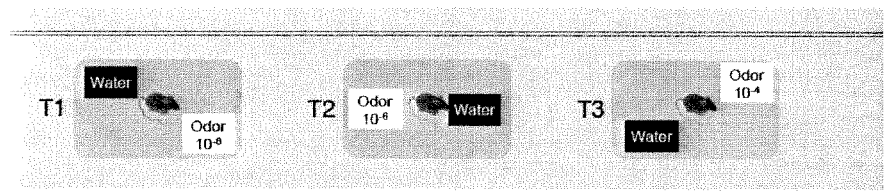
FIG. 1: Effect of rasagiline on odor detection threshold of wild type (WT) and mutant mice.
Figure 1:
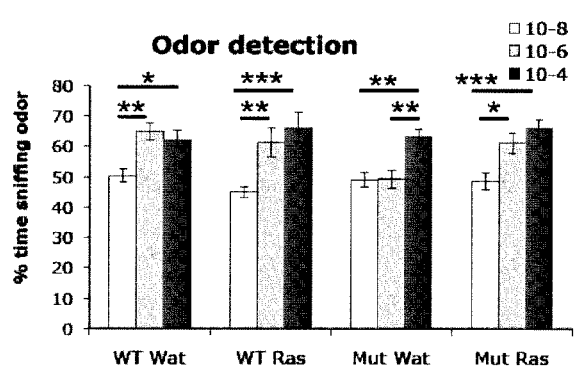
Figure 1:
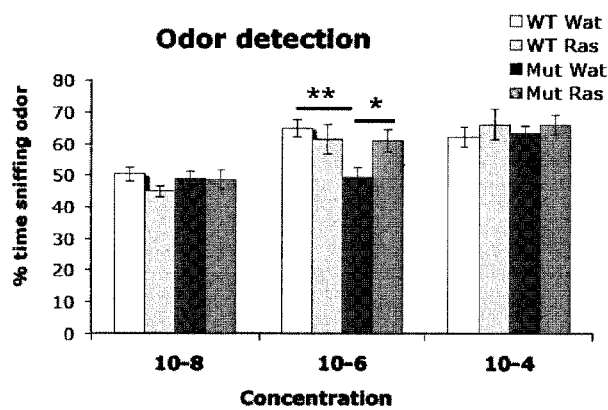

The subject invention provides a method of treating a symptom of olfactory dysfunction in a subject afflicted by olfactory dysfunction, the method comprising:

a) identifying the subject as afflicted by olfactory dysfunction, and
b) periodically administering to the subject so identified an amount of R(+)-N-propargyl-1-aminoindan or a pharmaceutically acceptable salt thereof, effective to treat the subject.

In an embodiment of the method, the subject is a non-Parkinson's disease subject.

The subject invention also provides a method of reducing the rate of progression of olfactory dysfunction in a non-Parkinson's disease subject afflicted by olfactory dysfunction, the method comprising periodically administering to the subject an amount of R(+)-N-propargyl-1-aminoindan or a pharmaceutically acceptable salt thereof effective to reduce the rate of progression of olfactory dysfunction in the non-Parkinson's disease subject.

The subject invention further provides a method of inhibiting loss of olfactory function in a non-Parkinson's disease subject, the method comprising periodically administering to the subject an amount of R(+)-N-propargyl-1-aminoindan or a pharmaceutically acceptable salt thereof effective to inhibit loss of olfactory function in the non-Parkinson's disease subject.

In an embodiment of the method, the amount of R(+)-N-propargyl-1-aminoindan or of the pharmaceutically acceptable salt thereof is from 0.01 mg to 5 mg per day.

In another embodiment of the method, the amount of R(+)-N-propargyl-1-aminoindan or of the pharmaceutically acceptable salt thereof is 0.5 mg per day.

In yet another embodiment of the method, the amount of R(+)-N-propargyl-1-aminoindan or of the pharmaceutically acceptable salt thereof is 2 mg per day.

In yet another embodiment of the method, the amount of R(+)-N-propargyl-1-aminoindan or of the pharmaceutically acceptable salt thereof is 1 mg per day.

In yet another embodiment of the method, R(+)-N-propargyl-1-aminoindan is administered in the form of free base.

In yet another embodiment of the method, the pharmaceutically acceptable salt of R(+)-N-propargyl-1-aminoindan is esylate, mesylate, sulphate, citrate or tartrate.

In yet another embodiment of the method, the pharmaceutically acceptable salt is a mesylate salt.

In yet another embodiment of the method, the pharmaceutically acceptable salt is a citrate salt.

In yet another embodiment of the method, the olfactory dysfunction is selected from the group consisting of anosmia, partial anosmia, hyposmia, hyperosmia, dysosmia, phantosmia, and olfactory agnosia.

In yet another embodiment of the method, the olfactory dysfunction is caused by a condition selected from the group consisting of head trauma, upper respiratory infection, toxic exposure, epilepsy, multiple sclerosis, Parkinson's disease, Alzheimer's disease, sinonasal disease, Addison's disease, Turner's syndrome, Cushing's syndrome, hypothyroidism, pseudohypoparathyroidism, Kallmann's syndrome and neoplasm.

In yet another embodiment of the method, the amount of R(+)-N-propargyl-1-aminoindan or a pharmaceutically acceptable salt thereof is formulated in oral, parenteral, rectal, or transdermal formulation.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2 . . . 49 mg unit amounts are included as embodiments of this invention.

As used herein, a Parkinson's disease (PD) patient is a patient who has been diagnosed with any of the following five PD stages described by Hoehn and Yahr (Hoehn M M, Yahr M D, Parkinsonism: onset, progression and mortality. Neurology 1967, 17:427-42).

Stage I: (mild or early disease): Symptoms affect only one side of the body.

Stage II: Both sides of the body are affected, but posture remains normal.

Stage III: (moderate disease): Both sides of the body are affected, and there is mild imbalance during standing or walking. However, the person remains independent.

Stage IV: (advanced disease): Both sides of the body are affected, and there is disabling instability while standing or walking. The person in this stage requires substantial help.

Stage V: Severe, fully developed disease is present. The person is restricted to a bed or chair.

As used herein, a "non-Parkinson's disease" patient is a patient who has not been diagnosed with any of the five PD stages described by Hoehn and Yahr.

As used herein, a "symptom of olfactory dysfunction" is one or more of the following:
a) decreased odor detection threshold;
b) decreased short-term olfactory memory;
c) decreased discriminating ability of a social odor;
d) decreased discriminating ability of a non-social odor.

As used herein, "functional decline" means the worsening of a symptom of olfactory dysfunction in a patient suffering from olfactory dysfunction over time.

As used herein, "reducing the rate of progression of olfactory dysfunction" means reducing the rate of progression of functional decline experienced by a patient suffering from olfactory dysfunction, as compared to the rate experienced by a patient suffering olfactory dysfunction and not receiving rasagiline over a period of time.

As used herein, a "pharmaceutically acceptable salt" of rasagiline includes citrate, tannate, malate, mesylate, maleate, fumarate, tartrate, esylate, p-toluenesulfonate, benzoate, acetate, phosphate and sulfate salts. For the preparation of pharmaceutically acceptable acid addition salts of the compounds of the invention, the free base can be reacted with the desired acids in the presence of a suitable solvent by conventional methods.

As used herein, an example of an immediate release formulation of rasagiline is an AZILECT® Tablet containing rasagiline mesylate.

Rasagiline can also be used in its free base form. A process of manufacture of the rasagiline base is described in PCT publication WO 2008/076348, the contents of which are hereby incorporated by reference.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

Specific examples of pharmaceutically acceptable carriers and excipients that may be used to formulate oral dosage forms of the present invention are described, e.g., in U.S. Pat. No. 6,126,968 to Peskin et al., issued Oct. 3, 2000. Techniques and compositions for making dosage forms useful in the present invention are described, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The pharmaceutical dosage forms may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration the invention provides suppositories with hydrophilic or hydrophobic vehicles; for topical application as ointments; and for transdermal delivery the invention provides suitable delivery systems as known in the art.

Tablets may contain suitable binders, lubricants, disintegrating agents, coloring agents, flavoring agents, flow-inducing agents, melting agents, stabilizing agents, solubilizing agents, antioxidants, buffering agent, chelating agents, fillers and plasticizers. For instance, for oral administration in the dosage unit form of a tablet or capsule, the active drug component can be combined with an oral, non-toxic, pharmaceutically acceptable, inert carrier such as gelatin, agar, starch, methyl cellulose, dicalcium phosphate, calcium sulfate, mannitol, sorbitol, microcrystalline cellulose and the like. Suitable binders include starch, gelatin, natural sugars such as corn starch, natural and synthetic gums such as acacia, tragacanth, or sodium alginate, povidone, carboxymethylcellulose, polyethylene glycol, waxes, and the like. Antioxidants include ascorbic acid, fumaric acid, citric acid, malic acid, gallic acid and its salts and esters, butylated hydroxyanisole, editic acid. Lubricants used in these dosage forms include sodium oleate, sodium stearate, sodium benzoate, sodium acetate, stearic acid, sodium stearyl fumarate, talc and the like. Disintegrators include, without limitation, starch, methyl cellulose, agar, bentonite, xanthan gum, croscarmellose sodium, sodium starch glycolate and the like, suitable plasticizers include triacetin, triethyl citrate, dibutyl sebacate, polyethylene glycol and the like.

One type of oral dosage forms of the present invention relates to delayed release formulations. Such formulations may be comprised of an acid resistant excipient which prevents the dosage form or parts thereof from contacting the acidic environment of the stomach. The acid resistant excipient may coat the rasagiline in the form of an enteric coated tablet, capsule, or gelatin capsule. Enteric coating, in the context of this invention, is a coating which prevents the dissolution of an active ingredient in the stomach. Specific examples of pharmaceutically acceptable carriers and excipients that may be used to formulate such delayed release formulations are described, e.g., in International Application Publication No. WO 06/014973, hereby incorporated by reference in its entirety.

Another type of oral dosage forms of the present invention relates to fast disintegrating formulations which provide a means to avoid the absorption of rasagiline in the stomach, and to eliminate the need for swallowing tablets, by absorption of rasagiline into the body before reaching the stomach. Such absorption of rasagiline can be accomplished by contact with the buccal, sublingual, pharyngeal and/or esophageal mucous membranes. To accomplish this, the fast disintegrating formulations were designed to rapidly disperse within the mouth to allow maximum contact of rasagiline with the buccal, sublingual, pharyngeal and/or esophageal mucous membranes. Specific examples of pharmaceutically acceptable carriers and excipients that may be used to formulate such fast disintegrating formulations are described, e.g., in International Application Publication No. WO 03/051338, hereby incorporated by reference in its entirety.

Other pharmaceutical compositions of the present invention include transdermal patches. Transdermal patches are medicated adhesive patches placed on the skin to deliver a time-released dose of medication through the skin and into the bloodstream. A wide variety of pharmaceuticals can be delivered through transdermal patches. Some pharmaceuticals must be combined with other substances, for example alcohol, to increase their ability to penetrate the skin. Transdermal patches have several important components, including a liner to protect the patch during storage, the drug, adhesive, a membrane (to control release of the drug from the reservoir), and a backing to protect the patch from the outer environment. The two most common types of transdermal patches are matrix and reservoir types. (Wikipedia; and Remington, The Science and Practice of Pharmacy, 20$^{th}$ Edition, 2000)

In reservoir type patches, a drug is combined with a non-volatile, inert liquid, such as mineral oil, whereas in matrix type patches a drug is dispersed in a lipophilic or hydrophilic polymer matrix such as acrylic or vinylic polymers. Adhesive polymers, such as polyisobutylene, are used to hold the patch in place on the skin. (Stanley Scheindlin, (2004) "Transdermal Drug Delivery: PAST, PRESENT, FUTURE," Molecular Interventions, 4:308-312)

The major limitation to transdermal drug-delivery is the intrinsic barrier property of the skin. Penetration enhancers are often added to transdermal drug formulations in order to disrupt the skin surface and cause faster drug delivery. Typical penetration enhancers include high-boiling alcohols, diols, fatty acid esters, oleic acid and glyceride-based solvents, and are commonly added at a concentration of one to 20 percent (w/w). (Melinda Hopp, "Developing Custom Adhesive Systems for Transdermal Drug Delivery Products," Drug Delivery)

This invention will be better understood from the experimental details which follow. However, one skilled in the art will readily appreciate that the specific methods and results discussed are merely illustrative of the invention as described more fully in the claims which follow thereafter.

Experimental Details

Study Design

Wild type (WT) and alpha-synuclein over-expressing (mutants) 11 months' males were treated with 3 mg/kg of rasagiline in the drinking water for eight weeks. Olfaction tests started four weeks after the beginning of the rasagiline treatment. The number of mice in each treatment group is summarized in table below.

|         | Treatment | |
|---------|-------|-----------|
| Mice    | Water | Rasagiline |
| Control | 21    | 18        |
| Mutant  | 19    | 20        |

Alpha-Synuclein Over-Expressing Mice

Transgenic mice overexpressing alpha-synuclein under the Thy1 promoter (Thy1-aSyn) have high levels of alpha-synuclein expression throughout the brain but no loss of nigrostriatal dopamine neurons up to 8 months. Thus, such mice are useful to model pre-clinical stages of PD, in particular, olfactory dysfunction which often precedes the onset of the cardinal motor symptoms of PD by several years and includes deficits in odor detection, discrimination and identification. Overexpression of alpha-synuclein is sufficient to cause olfactory deficits in mice similar to that observed in patients with PD (2).

The following olfaction tests were performed during the study:

1. Social odor discrimination test
2. Non-social odor discrimination test
3. Odor detection test
4. Short term olfactory memory test The following control tests were performed during the study:

1. Object exploration test
2. Object/odor discrimination test
3. Odor preference

EXAMPLE 1

Odor Detection Threshold Determination

This experiment was designed to determine whether rasagiline had positive effect on odor detection threshold of olfactory challenged animals (FIG. 1A). Odor detection threshold is the lowest concentration (dilution $10^{-8}$; $10^{-6}$; $10^{-4}$ in the water) at which mice are able to detect a novel odor. Upon detection of a novel odor, mice will spend more time sniffing it. The detection threshold was measured as percentage of time sniffing novel odor out of total time of sniffing.

Results:

The results of the experiment are summarized in tables 1a-1d. The analysis was performed by 2-way ANOVA followed by Bonferroni post-hoc test ($*p<0.05$, $p<0.01$, $*p<0.001$).

TABLE 1a

Odor detection threshold of WT untreated mice

| Treatment Group (n = 10) | | | % time sniffing odor at concentration: | | |
|---|---|---|---|---|---|
| Mice | Genotype | Treatment | $10^{-8}$ | $10^{-6}$ | $10^{-4}$ |
| 2  | WT | Water | 48.3 | 51.4 | 61.4 |
| 6  | WT | Water | 48.1 | 74.5 | 74.6 |
| 13 | WT | Water | 51.3 | 63.2 | 66.2 |
| 17 | WT | Water | 35.8 | 77.7 | 68.1 |
| 20 | WT | Water | 59.0 | 60.8 | 65.5 |
| 24 | WT | Water | 45.7 | 67.8 | 54.6 |
| 26 | WT | Water | 52.2 | 68.7 | 68.5 |
| 27 | WT | Water | 59.5 | 53.3 | 41.2 |

TABLE 1a-continued

Odor detection threshold of WT untreated mice

| Treatment Group (n = 10) | | | % time sniffing odor at concentration: | | |
|---|---|---|---|---|---|
| Mice | Genotype | Treatment | $10^{-8}$ | $10^{-6}$ | $10^{-4}$ |
| 31 | WT | Water | 49.7 | 60.1 | 67.4 |
| 35 | WT | Water | 53.5 | 71.9 | 55.0 |
| Mean | | | 50.3 | 64.9 | 62.2 |
| SEM | | | 2.2 | 2.8 | 3.0 |

TABLE 1b

Odor detection threshold of WT mice receiving rasagiline

| Treatment Group (n = 9) | | | % time sniffing odor at concentration: | | |
|---|---|---|---|---|---|
| Mice | Genotype | Treatment | $10^{-8}$ | $10^{-6}$ | $10^{-4}$ |
| 1 | WT | Ras | 38.4 | 44.4 | 70.2 |
| 5 | WT | Ras | 49.3 | 61.0 | 74.5 |
| 9 | WT | Ras | 48.3 | 56.1 | 74.4 |
| 12 | WT | Ras | 45.9 | 51.9 | 41.9 |
| 14 | WT | Ras | 52.7 | 83.5 | 86.4 |
| 18 | WT | Ras | 43.3 | 61.1 | 68.7 |
| 23 | WT | Ras | 39.1 | 82.5 | 56.0 |
| 33 | WT | Ras | 46.6 | 46.2 | 57.4 |
| 38 | WT | Ras | 40.4 | 64.9 | |
| Mean | | | 44.9 | 61.3 | 66.2 |
| SEM | | | 1.7 | 4.7 | 4.9 |

TABLE 1c

Odor detection threshold of untreated α-syn mutants

| Treatment: Group (n = 10) | | | % time sniffing odor at concentration: | | |
|---|---|---|---|---|---|
| Mice | Genotype | Treatment | $10^{-8}$ | $10^{-6}$ | $10^{-4}$ |
| 3 | Mutant | Water | 46.0 | 58.0 | 72.5 |
| 7 | Mutant | Water | 47.9 | 48.1 | 66.9 |
| 10 | Mutant | Water | 53.7 | 39.5 | 64.8 |
| 11 | Mutant | Water | 33.3 | 48.1 | 50.3 |
| 16 | Mutant | Water | 49.9 | 40.9 | 55.7 |
| 19 | Mutant | Water | 47.6 | 56.2 | 65.7 |
| 22 | Mutant | Water | 57.2 | 41.3 | 61.9 |
| 29 | Mutant | Water | 58.4 | 40.8 | 67.0 |
| 32 | Mutant | Water | 44.9 | 68.1 | 55.8 |
| 36 | Mutant | Water | 50.9 | 51.7 | 72.0 |
| Mean | | | 49.0 | 49.3 | 63.2 |
| SEM | | | 2.3 | 3.0 | 2.3 |

TABLE 1d

Odor detection threshold of α-syn mutants receiving rasagiline

| Treatment Group (n = 9) | | | % time sniffing odor at concentration: | | |
|---|---|---|---|---|---|
| Mice | Genotype | Treatment | $10^{-8}$ | $10^{-6}$ | $10^{-4}$ |
| 4 | Mutant | Ras | 43.7 | 60.2 | 73.6 |
| 8 | Mutant | Ras | 50.1 | 74.8 | 86.5 |
| 15 | Mutant | Ras | 40.9 | 50.0 | 62.2 |
| 21 | Mutant | Ras | 41.4 | 50.8 | 66.6 |
| 25 | Mutant | Ras | 64.4 | 54.1 | 57.7 |
| 28 | Mutant | Ras | 58.3 | 56.9 | 67.4 |
| 30 | Mutant | Ras | 50.5 | 60.2 | 60.7 |
| 34 | Mutant | Ras | 38.8 | 80.6 | 55.7 |
| 37 | Mutant | Ras | 49.8 | 62.8 | 62.7 |

TABLE 1d-continued

Odor detection threshold of α-syn mutants receiving rasagiline

| Treatment Group (n = 9) | | | % time sniffing odor at concentration: | | |
|---|---|---|---|---|---|
| Mice | Genotype | Treatment | $10^{-8}$ | $10^{-6}$ | $10^{-4}$ |
| Mean | | | 48.7 | 61.1 | 65.9 |
| SEM | | | 2.8 | 3.5 | 3.2 |

Discussion:

The results above demonstrate that rasagiline improved the odor threshold of α-syn mutants from $10^{-4}$ to $10^{6}$ (FIG. 1B). The data in FIG. 1B were analyzed by 2-way ANOVA with Effect of the concentration $p<0.001$; No effect of the group $p>0.05$; No interaction conc *group $p>0.05$; and Bonferroni post-hoc (*$p<0.05$, $p<0.01$ and *$p<0.001$). FIG. 1B shows that mutants need a higher concentration ($10^{-4}$) to detect the odor compared to controls ($10^{-6}$) and that rasagiline improves the odor detection threshold of mutants.

The results above also demonstrate that at the concentration of $10^{-6}$, rasagiline improved the odor detection ability of α-syn mutants (FIG. 1C). The data in FIG. 1C were analyzed by 2-way ANOVA with Bonferroni post-hoc, *$p<0.05$, **$p<0.01$; At $10^{-8}$: No effect of genotype and treatment, No interaction genotype*treat; At $10^{-6}$: No effect treatment, Effect of genotype and interaction genotype*treat $p<0.05$; and At $10^{-4}$: No effect of genotype and treatment, No interaction genotype*treat. FIG. 1C shows that at the concentration $10^{-6}$, untreated mutants don't detect the odor and rasagiline improves the odor detection ability of mutants.

EXAMPLE 2

Short-Term Olfactory Memory

Figure 2:
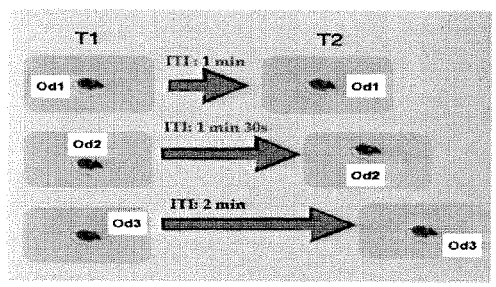
FIG. 2: Effect of rasagiline on short-term olfactory memory.
Figure 2:
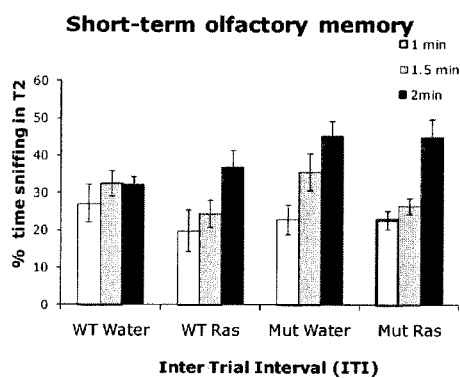
Figure 2:
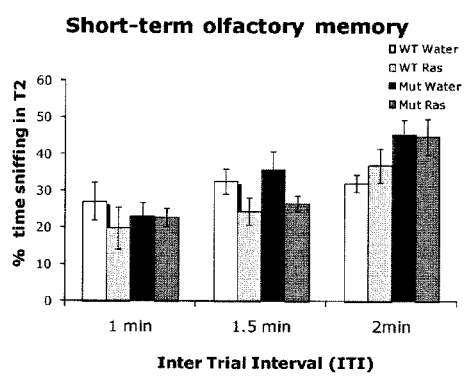

This experiment was designed to assess the effect of rasagiline on the capability of the mutant animals to remember a novel odor during a short time interval of 1 min, 1 min 30 s or 2 min (FIG. 2A). The underlying principle was that if mice would spend less time sniffing the odor at T2 (second exposure to the odor) their short term olfactory memory is intact. The testing parameter was percentage of time of sniffing at T2, calculated as time of sniffing at T2 out of total time of sniffing at T1 (first exposure) & T2.

Results:

The results of the experiment are summarized in tables 2a-2d. The analysis was performed by 2-way ANOVA followed by Bonferroni post-hoc, or by a non parametric test, Kruskal-Wallis, when the normal distribution failed.

TABLE 2a

Short-term olfactory memory of WT untreated mice

| Treatment Group (n = 10) | | | % time sniffing during T2 after interval: | | |
|---|---|---|---|---|---|
| Mice | Genotype | Treatment | 1 Min | 1.5 min | 2 min |
| 2-2 | WT | Water | 35.4 | 25.9 | 37.1 |
| 2-6 | WT | Water | 36.6 | 20.1 | 19.6 |
| 2-13 | WT | Water | 46.7 | 53.5 | 19.6 |
| 2-17 | WT | Water | 12.9 | 28.6 | 37.2 |
| 2-20 | WT | Water | 8.8 | 39.1 | 34.8 |
| 2-24 | WT | Water | 46.8 | 42.7 | 33.8 |
| 2-26 | WT | Water | 41.0 | 33.6 | 36.1 |
| 2-27 | WT | Water | 11.2 | 35.6 | 27.0 |

TABLE 2a-continued

Short-term olfactory memory of WT untreated mice

| Mice | Treatment Group (n = 10) | | % time sniffing during T2 after interval: | | |
|---|---|---|---|---|---|
| | Genotype | Treatment | 1 Min | 1.5 min | 2 min |
| 2-31 | WT | Water | 8.0 | 26.5 | 39.7 |
| 2-35 | WT | Water | 24.0 | 19.3 | 35.5 |
| Mean | | | 27.1 | 32.5 | 32.0 |
| SEM | | | 5.0 | 3.4 | 2.3 |

TABLE 2b

Short-term olfactory memory of WT mice receiving rasagiline

| Mice | Treatment Group (n = 9) | | % time sniffing during T2 after interval: | | |
|---|---|---|---|---|---|
| | Genotype | Treatment | 1 min | 1.5 min | 2 min |
| 2-1 | WT | Ras | 18.8 | 8.6 | 19.9 |
| 2-5 | WT | Ras | 44.9 | 23.4 | 59.2 |
| 2-9 | WT | Ras | 47.6 | 20.4 | 25.5 |
| 2-12 | WT | Ras | 2.3 | 34.4 | 27.9 |
| 2-14 | WT | Ras | 7.6 | 19.4 | 33.3 |
| 2-18 | WT | Ras | 3.3 | 29.8 | 58.3 |
| 2-23 | WT | Ras | 28.0 | 32.5 | 31.6 |
| 2-33 | WT | Ras | 13.2 | 41.4 | 41.0 |
| 2-38 | WT | Ras | 12.7 | 10.4 | 36.0 |
| Mean | | | 19.8 | 24.5 | 37.0 |
| SEM | | | 5.6 | 3.7 | 4.6 |

TABLE 2c

Short-term olfactory memory of untreated α-syn mutants

| Mice | Treatment Group 2 (n = 10) | | % time sniffing during T2 after interval: | | |
|---|---|---|---|---|---|
| | Genotype | Treatment | 1 min | 1.5 min | 2 min |
| 2-3 | Mutant | Water | 2.6 | 36.8 | 30.6 |
| 2-7 | Mutant | Water | 13.7 | 23.3 | 48.9 |
| 2-10 | Mutant | Water | 18.3 | 23.2 | 55.6 |
| 2-11 | Mutant | Water | 24.0 | 23.1 | 67.1 |
| 2-16 | Mutant | Water | 38.1 | 36.8 | 57.4 |
| 2-19 | Mutant | Water | 46.0 | 31.0 | 45.9 |
| 2-22 | Mutant | Water | 18.6 | 29.0 | 50.3 |
| 2-29 | Mutant | Water | 21.4 | 75.6 | 32.6 |
| 2-32 | Mutant | Water | 27.5 | 33.9 | 30.1 |
| 2-36 | Mutant | Water | 19.5 | 44.3 | 34.0 |
| Mean | | | 23.0 | 35.7 | 45.2 |
| SEM | | | 3.9 | 5.0 | 4.1 |

TABLE 2d

Short-term olfactory memory of α-syn mutants receiving rasagiline

| Mice | Treatment Group 2 (n = 9) | | % time sniffing during T2 after interval: | | |
|---|---|---|---|---|---|
| | Genotype | Treatment | 1 min | 1.5 min | 2 min |
| 2-4 | Mutant | Ras | 19.1 | 28.6 | 52.8 |
| 2-8 | Mutant | Ras | 22.9 | 40.9 | 44.1 |
| 2-15 | Mutant | Ras | 20.1 | 27.7 | 25.7 |
| 2-21 | Mutant | Ras | 30.1 | 19.2 | 51.8 |
| 2-25 | Mutant | Ras | 26.4 | 25.2 | 22.7 |
| 2-28 | Mutant | Ras | 37.8 | 23.3 | 38.1 |
| 2-30 | Mutant | Ras | 16.7 | 26.6 | 67.2 |

TABLE 2d-continued

Short-term olfactory memory of α-syn mutants receiving rasagiline

| Mice | Treatment Group 2 (n = 9) | | % time sniffing during T2 after interval: | | |
|---|---|---|---|---|---|
| | Genotype | Treatment | 1 min | 1.5 min | 2 min |
| 2-34 | Mutant | Ras | 13.4 | 20.2 | 56.8 |
| 2-37 | Mutant | Ras | 17.9 | 27.5 | 44.4 |
| Mean | | | 22.7 | 26.6 | 44.8 |
| SEM | | | 2.5 | 2.1 | 4.8 |

Discussion:

The results above demonstrate that rasagiline has positive effect on short term olfactory memory of WT and of α-syn mutants mice, in particular at the 1.5 min interval (FIGS. 2B&C).

The data in FIG. 2B were analyzed by 2-way ANOVA with Effect of ITI $p<0.001$; No effect of the group $p>0.05$; No Interaction ITI*group $p>0.05$; and Bonferroni post-hoc (*$p<0.05$, $p<0.01$, *$p<0.001$). FIG. 2B shows that that at ITI of 2 min, mutants and WT-Ras showed a reduced short-term olfactory memory compared to WT-water.

The data in FIG. 2C were analyzed by 2-way ANOVA followed by Bonferroni post-hoc, *$p>0.05$ at 1 min and 2 min and by a non parametric test, Kruskal-Wallis, at 1.5 min; At 1 min: No effect of genotype and treatment, No interaction genotype*treat; At 1.5 min: no statistical difference between groups, $p>0.05$, Effect of treatment $p<0.05$, No effect of genotype and no interaction genotype*treat; and At 2 min: Effect of genotype $p<0.05$, No effect of genotype and no interaction genotype*treat. FIG. 22 shows that at 1.5 min, rasagiline had a positive effect on short term olfactory memory for both WT and mutants.

EXAMPLE 3

Social Odor Discrimination

Figure 3:
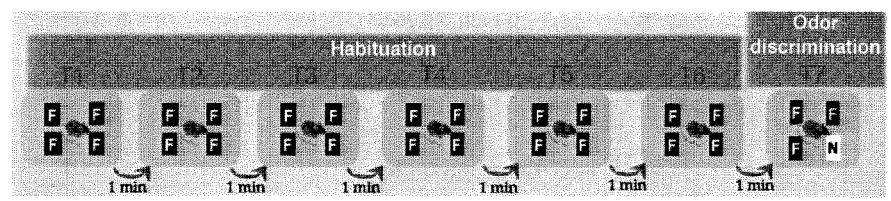
FIG. 3: Effect of rasagiline on the ability of WT and mutant mice to discriminate between familiar and novel social odors.
Figure 3:
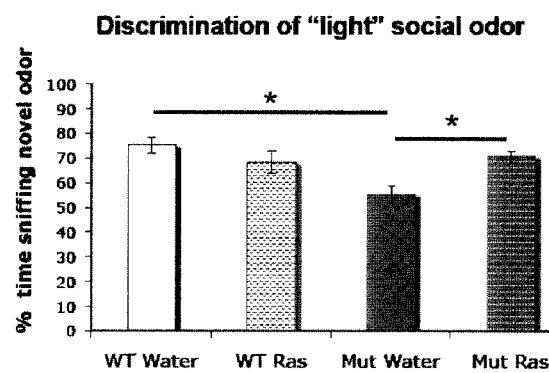
Figure 3:
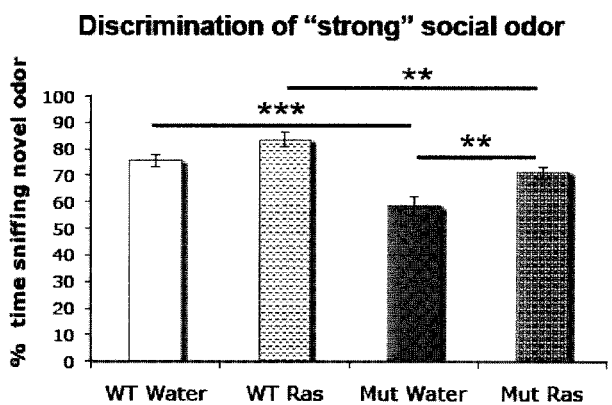

This experiment was designed to assess effect of rasagiline on the capability of the mice to discriminate between a familiar social odor (F) and a novel social odor (N) (FIG. 3A). Mice capable of discriminating between the odors would spend more time sniffing the new odor. The experiment was further subdivided into two levels of odor intensity:
Light intensity: two days of odor impregnation
Strong intensity: seven days of odor impregnation
The testing parameter was percentage of time of sniffing novel odor out of total time of sniffing.
Results:
1. Discrimination of Light Social Odors:
The results of the experiment are summarized in tables 3a-3d. The analysis was performed a non parametric test, Kruskal-Wallis, and Mann-Whitney test was used as post-hoc (***$p<0.001$).

TABLE 3a

Discrimination of light social odors by WT untreated mice

| Mice (n = 21) | Genotype | Treatment | Time Sniffing F | Time Sniffing N | Total time sniffing | % time sniffing N |
|---|---|---|---|---|---|---|
| 1-2 | WT | Water | 2.9 | 7.3 | 10.2 | 71.4 |
| 1-6 | WT | Water | 17.6 | 39.3 | 56.9 | 69.1 |
| 1-13 | WT | Water | 1.7 | 6.1 | 7.8 | 78.2 |
| 1-17 | WT | Water | 12.0 | 4.2 | 16.2 | 25.7 |
| 1-20 | WT | Water | 4.3 | 21.5 | 25.8 | 83.5 |

TABLE 3a-continued

Discrimination of light social odors by WT untreated mice

| Mice (n = 21) | Genotype | Treatment | Time Sniffing F | Time Sniffing N | Total time sniffing | % time sniffing N |
|---|---|---|---|---|---|---|
| 1-24 | WT | Water | 8.0 | 6.1 | 14.1 | 43.3 |
| 1-26 | WT | Water | 3.9 | 15.6 | 19.5 | 80.0 |
| 1-27 | WT | Water | 3.5 | 10.8 | 14.3 | 75.3 |
| 1-31 | WT | Water | 12.4 | 42.7 | 55.1 | 77.6 |
| 1-35 | WT | Water | 2.4 | 13.8 | 16.2 | 85.3 |
| 2-2 | WT | Water | 3.8 | 13.4 | 17.2 | 77.9 |
| 2-6 | WT | Water | 7.1 | 60.8 | 67.9 | 89.5 |
| 2-16 | WT | Water | 2.2 | 13.7 | 15.9 | 86.2 |
| 2-19 | WT | Water | 2.6 | 8.9 | 11.5 | 77.3 |
| 2-20 | WT | Water | 8.4 | 31.1 | 39.5 | 78.8 |
| 2-22 | WT | Water | 5.3 | 46.6 | 51.9 | 89.8 |
| 2-24 | WT | Water | 6.3 | 15.9 | 22.2 | 71.6 |
| 2-28 | WT | Water | 1.4 | 61.9 | 63.2 | 97.8 |
| 2-31 | WT | Water | 4.8 | 17.6 | 22.4 | 78.5 |
| 2-34 | WT | Water | 4.0 | 12.4 | 16.4 | 75.6 |
| 2-35 | WT | Water | 12.5 | 25.7 | 38.2 | 67.3 |
|  | Mean |  | 6.0 | 22.6 | 28.7 | 75.2 |
|  | SEM |  | 0.9 | 3.9 | 4.2 | 3.4 |

TABLE 3b

Discrimination of light social odors by WT mice receiving rasagiline

| Mice (n = 18) | Genotype | Treatment | Time Sniffing F | Time Sniffing N | Total time sniffing | % time sniffing N |
|---|---|---|---|---|---|---|
| 1-1 | WT | Rasagiline | 2.9 | 4.2 | 7.1 | 59.2 |
| 1-5 | WT | Rasagiline | 8.5 | 10.7 | 19.1 | 55.9 |
| 1-9 | WT | Rasagiline | 2.2 | 60.0 | 62.2 | 96.5 |
| 1-12 | WT | Rasagiline | 1.9 | 7.4 | 9.3 | 79.2 |
| 1-14 | WT | Rasagiline | 6.3 | 3.7 | 10.0 | 37.2 |
| 1-18 | WT | Rasagiline | 4.8 | 6.2 | 11.0 | 56.4 |
| 1-23 | WT | Rasagiline | 5.8 | 21.6 | 27.4 | 78.8 |
| 1-33 | WT | Rasagiline | 7.9 | 7.1 | 15.0 | 47.4 |
| 1-38 | WT | Rasagiline | 7.3 | 21.6 | 28.9 | 74.7 |
| 2-1 | WT | Rasagiline | 3.6 | 36.2 | 39.8 | 91.0 |
| 2-5 | WT | Rasagiline | 4.5 | 16.8 | 21.3 | 78.9 |
| 2-17 | WT | Rasagiline | 2.8 | 7.6 | 10.4 | 73.0 |
| 2-18 | WT | Rasagiline | 39.8 | 56.5 | 96.3 | 58.7 |
| 2-23 | WT | Rasagiline | 3.9 | 17.2 | 21.1 | 81.5 |
| 2-29 | WT | Rasagiline | 2.1 | 18.1 | 20.2 | 89.6 |
| 2-33 | WT | Rasagiline | 6.7 | 2.9 | 9.6 | 30.5 |
| 2-36 | WT | Rasagiline | 4.8 | 36.7 | 41.5 | 88.4 |
| 2-37 | WT | Rasagiline | 6.2 | 7.2 | 13.4 | 53.6 |
|  | Mean |  | 6.8 | 19.0 | 25.8 | 68.4 |
|  | SEM |  | 2.0 | 4.1 | 5.3 | 4.5 |

TABLE 3c

Discrimination of light social odors by untreated α-syn mutants

| Mice (n = 19) | Genotype | Treatment | Time Sniffing F | Time Sniffing N | Total time sniffing | % time sniffing N |
|---|---|---|---|---|---|---|
| 1-3 | Mutant | Water | 3.6 | 4.9 | 8.5 | 58.0 |
| 1-7 | Mutant | Water | 3.8 | 3.8 | 7.6 | 50.3 |
| 1-10 | Mutant | Water | 3.0 | 6.1 | 9.1 | 66.8 |
| 1-11 | Mutant | Water | 2.2 | 3.3 | 5.5 | 60.6 |
| 1-16 | Mutant | Water | 2.6 | 4.8 | 7.4 | 64.7 |
| 1-19 | Mutant | Water | 6.3 | 6.7 | 12.9 | 51.5 |
| 1-22 | Mutant | Water | 2.6 | 14.0 | 16.6 | 84.3 |
| 1-29 | Mutant | Water | 3.2 | 3.7 | 6.9 | 53.4 |
| 1-32 | Mutant | Water | 2.4 | 2.6 | 5.1 | 51.9 |
| 1-36 | Mutant | Water | 6.3 | 1.0 | 7.3 | 13.6 |
| 2-3 | Mutant | Water | 5.0 | 4.7 | 9.7 | 48.2 |
| 2-7 | Mutant | Water | 11.6 | 60.2 | 71.8 | 83.9 |
| 2-11 | Mutant | Water | 4.6 | 3.4 | 8.0 | 42.6 |
| 2-12 | Mutant | Water | 5.0 | 9.8 | 14.8 | 66.2 |
| 2-13 | Mutant | Water | 5.3 | 4.3 | 9.6 | 45.0 |
| 2-26 | Mutant | Water | 4.2 | 4.9 | 9.1 | 53.9 |
| 2-27 | Mutant | Water | 3.0 | 3.7 | 6.7 | 55.1 |
| 2-39 | Mutant | Water | 5.3 | 6.5 | 11.8 | 54.9 |
| 2-40 | Mutant | Water | 6.1 | 5.6 | 11.7 | 47.9 |
|  | Mean |  | 4.5 | 8.1 | 12.6 | 55.4 |
|  | SEM |  | 0.5 | 3.0 | 3.4 | 3.5 |

TABLE 3d

Discrimination of light social odors α-syn mutants receiving rasagiline

| Mice (n = 20) | Genotype | Treatment | Time Sniffing F | Time Sniffing N | Total time sniffing | % time sniffing N |
|---|---|---|---|---|---|---|
| 1-4 | Mutant | Rasagiline | 1.0 | 6.4 | 7.4 | 86.4 |
| 1-8 | Mutant | Rasagiline | 3.3 | 8.3 | 11.6 | 71.3 |
| 1-15 | Mutant | Rasagiline | 2.8 | 5.8 | 8.6 | 67.8 |
| 1-21 | Mutant | Rasagiline | 3.1 | 5.8 | 8.9 | 65.5 |
| 1-25 | Mutant | Rasagiline | 3.6 | 6.6 | 10.2 | 64.7 |
| 1-28 | Mutant | Rasagiline | 2.4 | 3.5 | 5.9 | 59.6 |
| 1-30 | Mutant | Rasagiline | 3.1 | 6.6 | 9.7 | 68.3 |
| 1-34 | Mutant | Rasagiline | 2.2 | 4.9 | 7.2 | 68.8 |
| 1-37 | Mutant | Rasagiline | 2.7 | 14.6 | 17.3 | 84.3 |
| 2-4 | Mutant | Rasagiline | 5.2 | 9.1 | 14.3 | 63.6 |
| 2-8 | Mutant | Rasagiline | 2.5 | 12.9 | 15.4 | 83.8 |
| 2-9 | Mutant | Rasagiline | 3.4 | 8.4 | 11.8 | 71.1 |
| 2-10 | Mutant | Rasagiline | 2.4 | 12.0 | 14.4 | 83.3 |
| 2-14 | Mutant | Rasagiline | 2.0 | 1.6 | 3.6 | 44.4 |
| 2-15 | Mutant | Rasagiline | 3.2 | 11.4 | 14.6 | 78.0 |
| 2-21 | Mutant | Rasagiline | 3.4 | 6.6 | 10.0 | 65.9 |
| 2-25 | Mutant | Rasagiline | 5.8 | 14.5 | 20.3 | 71.4 |
| 2-30 | Mutant | Rasagiline | 2.1 | 6.8 | 8.9 | 76.5 |
| 2-32 | Mutant | Rasagiline | 5.1 | 10.8 | 15.9 | 67.9 |
| 2-38 | Mutant | Rasagiline | 2.5 | 6.9 | 9.4 | 73.4 |
|  | Mean |  | 3.1 | 8.2 | 11.3 | 70.8 |
|  | SEM |  | 0.3 | 0.8 | 0.9 | 2.2 |

2. Discrimination of Strong Social Odors:

The results of the experiment are summarized in tables 3e-3h. The analysis was performed by 2-way ANOVA.

TABLE 3e

Discrimination of strong social odors by WT untreated mice

| Mice (n = 21) | Genotype | Treatment | Time Sniffing F | Time Sniffing N | Total time sniffing | % time sniffing N |
|---|---|---|---|---|---|---|
| 1-2 | WT | Water | 4.4 | 10.1 | 14.5 | 69.8 |
| 1-6 | WT | Water | 9.5 | 16.6 | 26.0 | 63.7 |
| 1-13 | WT | Water | 3.2 | 7.0 | 10.2 | 68.9 |
| 1-17 | WT | Water | 7.9 | 27.2 | 35.0 | 77.5 |
| 1-20 | WT | Water | 10.2 | 27.7 | 37.9 | 73.2 |
| 1-24 | WT | Water | 8.7 | 15.6 | 24.4 | 64.2 |
| 1-26 | WT | Water | 13.2 | 49.8 | 63.1 | 79.0 |
| 1-27 | WT | Water | 0.2 | 76.7 | 76.9 | 99.7 |
| 1-31 | WT | Water | 3.9 | 68.1 | 72.0 | 94.6 |
| 1-35 | WT | Water | 3.4 | 7.4 | 10.7 | 68.8 |
| 2-2 | WT | Water | 4.0 | 21.4 | 25.4 | 84.3 |
| 2-6 | WT | Water | 6.8 | 14.2 | 21.0 | 67.6 |
| 2-16 | WT | Water | 3.9 | 13.6 | 17.5 | 77.7 |
| 2-19 | WT | Water | 2.8 | 12.5 | 15.3 | 82.0 |
| 2-20 | WT | Water | 5.4 | 10.0 | 15.4 | 65.1 |
| 2-22 | WT | Water | 6.1 | 14.6 | 20.7 | 70.5 |
| 2-24 | WT | Water | 7.8 | 8.9 | 16.7 | 53.4 |

TABLE 3e-continued

Discrimination of strong social odors by WT untreated mice

| Mice (n = 21) | Genotype | Treatment | Time Sniffing F | Time Sniffing N | Total time sniffing | % time sniffing N |
|---|---|---|---|---|---|---|
| 2-28 | WT | Water | 8.2 | 56.1 | 64.3 | 87.2 |
| 2-31 | WT | Water | 11.6 | 31.2 | 42.8 | 72.9 |
| 2-34 | WT | Water | 2.5 | 10.8 | 13.3 | 81.4 |
| 2-35 | WT | Water | 3.5 | 22.5 | 26.0 | 86.6 |
|  | Mean |  | 6.0 | 24.9 | 30.9 | 75.6 |
|  | SEM |  | 0.7 | 4.5 | 4.6 | 2.4 |

TABLE 3f

Discrimination of strong social odors by WT mice receiving rasagiline

| Mice (n = 18) | Genotype | Treatment | Time Sniffing F | Time Sniffing N | Total time sniffing | % time sniffing N |
|---|---|---|---|---|---|---|
| 1-1 | WT | Rasagiline | 4.0 | 26.1 | 30.0 | 86.8 |
| 1-5 | WT | Rasagiline | 5.9 | 36.2 | 42.2 | 86.0 |
| 1-9 | WT | Rasagiline | 1.9 | 20.8 | 22.6 | 91.8 |
| 1-12 | WT | Rasagiline | 2.1 | 11.7 | 13.9 | 84.7 |
| 1-14 | WT | Rasagiline | 1.2 | 45.7 | 46.8 | 97.5 |
| 1-18 | WT | Rasagiline | 4.7 | 6.0 | 10.7 | 56.4 |
| 1-23 | WT | Rasagiline | 5.3 | 34.1 | 39.5 | 86.5 |
| 1-33 | WT | Rasagiline | 2.8 | 60.9 | 63.7 | 95.6 |
| 1-38 | WT | Rasagiline | 8.9 | 36.6 | 45.5 | 80.4 |
| 2-1 | WT | Rasagiline | 4.7 | 28.8 | 33.5 | 86.0 |
| 2-5 | WT | Rasagiline | 5.1 | 14.1 | 19.2 | 73.3 |
| 2-17 | WT | Rasagiline | 4.5 | 21.0 | 25.5 | 82.5 |
| 2-18 | WT | Rasagiline | 21.4 | 25.1 | 46.5 | 54.0 |
| 2-23 | WT | Rasagiline | 5.9 | 37.9 | 43.8 | 86.5 |
| 2-29 | WT | Rasagiline | 3.2 | 48.7 | 51.9 | 93.8 |
| 2-33 | WT | Rasagiline | 0.9 | 3.9 | 4.8 | 81.1 |
| 2-36 | WT | Rasagiline | 6.7 | 60.4 | 67.1 | 90.0 |
| 2-37 | WT | Rasagiline | 1.7 | 12.1 | 13.8 | 87.7 |
|  | Mean |  | 5.0 | 29.5 | 34.5 | 83.4 |
|  | SEM |  | 1.1 | 4.0 | 4.3 | 2.8 |

TABLE 3g

Discrimination of strong social odors by untreated α-syn mutants

| Mice (n = 19) | Genotype | Treatment | Time Sniffing F | Time Sniffing N | Total time sniffing | % time sniffing N |
|---|---|---|---|---|---|---|
| 1-3 | Mutant | Water | 4.0 | 1.6 | 5.6 | 29.2 |
| 1-7 | Mutant | Water | 2.4 | 2.7 | 5.0 | 53.1 |
| 1-10 | Mutant | Water | 1.5 | 4.2 | 5.7 | 73.6 |
| 1-11 | Mutant | Water | 2.4 | 3.3 | 5.6 | 58.0 |
| 1-16 | Mutant | Water | 2.5 | 3.7 | 6.1 | 60.1 |
| 1-19 | Mutant | Water | 1.8 | 2.7 | 4.5 | 60.5 |
| 1-22 | Mutant | Water | 5.0 | 10.2 | 15.2 | 67.3 |
| 1-29 | Mutant | Water | 2.9 | 4.0 | 6.9 | 58.3 |
| 1-32 | Mutant | Water | 4.6 | 13.8 | 18.4 | 74.9 |
| 1-36 | Mutant | Water | 2.8 | 3.4 | 6.3 | 55.0 |
| 2-3 | Mutant | Water | 5.6 | 6.7 | 12.3 | 54.4 |
| 2-7 | Mutant | Water | 7.5 | 24.4 | 31.9 | 76.5 |
| 2-11 | Mutant | Water | 2.4 | 9.6 | 12.0 | 79.9 |
| 2-12 | Mutant | Water | 2.0 | 10.3 | 12.3 | 83.8 |
| 2-13 | Mutant | Water | 5.8 | 5.3 | 11.1 | 47.7 |
| 2-26 | Mutant | Water | 6.5 | 2.5 | 9.0 | 27.7 |
| 2-27 | Mutant | Water | 4.4 | 3.4 | 7.8 | 43.5 |
| 2-39 | Mutant | Water | 4.7 | 4.5 | 9.2 | 49.1 |
| 2-40 | Mutant | Water | 1.4 | 2.1 | 3.5 | 60.0 |
|  | Mean |  | 3.7 | 6.2 | 9.9 | 58.6 |
|  | SEM |  | 0.4 | 1.3 | 1.5 | 3.5 |

TABLE 3h

Discrimination of strong social odors α-syn mutants receiving rasagiline

| Mice (n = 20) | Genotype | Treatment | Time Sniffing F | Time Sniffing N | Total time sniffing | % time sniffing N |
|---|---|---|---|---|---|---|
| 1-4 | Mutant | Rasagiline | 3.66 | 3.36 | 7.0 | 47.9 |
| 1-8 | Mutant | Rasagiline | 6.98 | 6.04 | 13.0 | 46.4 |
| 1-15 | Mutant | Rasagiline | 2.28 | 4.87 | 7.2 | 68.1 |
| 1-21 | Mutant | Rasagiline | 1.62 | 3.21 | 4.8 | 66.5 |
| 1-25 | Mutant | Rasagiline | 2.96 | 6.47 | 9.4 | 68.6 |
| 1-28 | Mutant | Rasagiline | 2.60 | 5.92 | 8.5 | 69.5 |
| 1-30 | Mutant | Rasagiline | 5.02 | 12.57 | 17.6 | 71.5 |
| 1-34 | Mutant | Rasagiline | 2.00 | 5.65 | 7.7 | 73.9 |
| 1-37 | Mutant | Rasagiline | 3.12 | 8.64 | 11.8 | 73.5 |
| 2-4 | Mutant | Rasagiline | 2.1 | 4.3 | 6.4 | 66.7 |
| 2-8 | Mutant | Rasagiline | 5.0 | 36.0 | 41.0 | 87.8 |
| 2-9 | Mutant | Rasagiline | 2.2 | 5.3 | 7.4 | 70.9 |
| 2-10 | Mutant | Rasagiline | 3.0 | 18.1 | 21.1 | 85.8 |
| 2-14 | Mutant | Rasagiline | 3.0 | 5.2 | 8.2 | 63.4 |
| 2-15 | Mutant | Rasagiline | 1.8 | 4.0 | 5.8 | 69.6 |
| 2-21 | Mutant | Rasagiline | 2.4 | 6.8 | 9.2 | 74.0 |
| 2-25 | Mutant | Rasagiline | 1.8 | 5.3 | 7.0 | 74.9 |
| 2-30 | Mutant | Rasagiline | 3.3 | 7.1 | 10.4 | 68.4 |
| 2-32 | Mutant | Rasagiline | 4.5 | 29.8 | 34.3 | 86.9 |
| 2-38 | Mutant | Rasagiline | 3.6 | 7.1 | 10.7 | 66.2 |
|  | Mean |  | 3.1 | 9.3 | 12.4 | 70.0 |
|  | SEM |  | 0.3 | 2.0 | 2.1 | 2.3 |

Discussion:

Discrimination of Light Social Odor Intensity:

The results above demonstrate that rasagiline improves discrimination of light social odor in α-syn mutants mice (FIG. 3B). The data in FIG. 3B were analyzed with Kruskal Wallis ($p<0.001$) and Mann-Whitney post-hoc (***$p<0.001$). FIG. 3B shows that mutants are impaired to discriminate "light" social odor and rasagiline improves the discrimination of social odor in mutants.

Discrimination of Strong Social Odor Intensity:

The results above also demonstrate that rasagiline improves discrimination of strong social odor in WT and α-syn mutants mice (FIG. 3C). The data in FIG. 3C were analyzed by 2-way ANOVA with Effect of the genotype $p<0.001$; Effect of the treatment $p<0.001$; No interaction genotype*treatment $p>0.05$; and Bonferroni post-hoc, $p<0.01$, *$p<0.001$. FIG. 3C shows that mutants are impaired to discriminate "strong" social odor and rasagiline improves the discrimination of strong social odor in mice.

EXAMPLE 4

Non-Social Odor Discrimination

Figure 4:
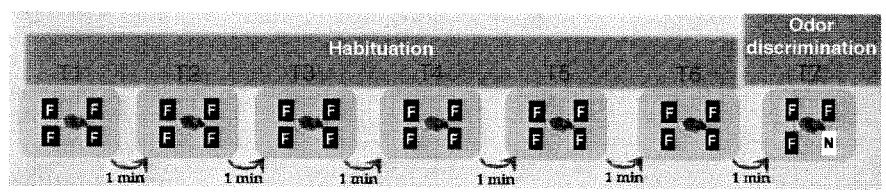
FIG. 4: Effect of rasagiline on the ability of WT and mutant mice to discriminate between two close non-social odors.
Figure 4:
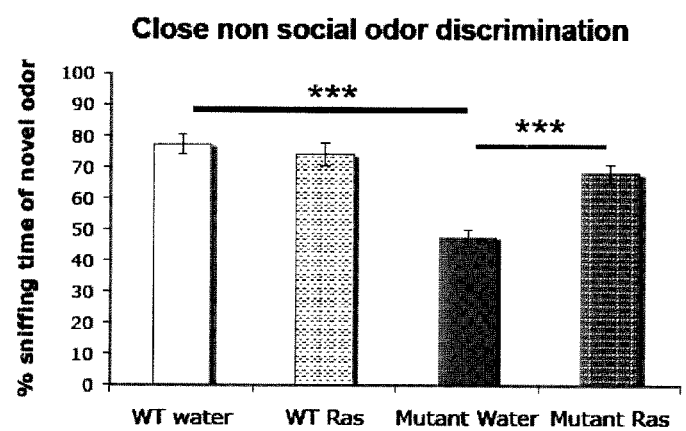

This experiment was designed to assess effect of rasagiline on the capability of mice to discriminate between two close non-social odors. In this experiment, lemon odor served as a familiar odor (F), and lime—as a novel odor (N) (FIG. 4A). Mice capable of discriminating between the odors will spend more time sniffing the new odor. The testing parameter was percentage of time of sniffing novel odor out of total time of sniffing.

Results:

The results of the experiment are summarized in tables 4a-4d. The analysis was performed by 2-way ANOVA and Bonferroni post-hoc.

TABLE 4a

Discrimination of non-social odors by WT untreated mice

| Mice (n = 20) | Genotype | Treatment | Time Sniffing F | Time Sniffing N | Total time sniffing | % time sniffing N |
|---|---|---|---|---|---|---|
| 1-2 | WT | Water | 1.5 | 12.6 | 14.1 | 89.4 |
| 1-6 | WT | Water | 3.7 | 49.9 | 53.6 | 93.1 |
| 1-16 | WT | Water | 12.0 | 32.8 | 44.8 | 73.2 |
| 1-19 | WT | Water | 14.8 | 41.6 | 56.4 | 73.8 |
| 1-20 | WT | Water | 6.5 | 10.9 | 17.4 | 62.5 |
| 1-22 | WT | Water | 11.6 | 22.8 | 34.4 | 66.2 |
| 1-24 | WT | Water | 3.0 | 10.8 | 13.8 | 78.2 |
| 1-28 | WT | Water | 5.6 | 43.0 | 48.6 | 88.5 |
| 1-31 | WT | Water | 10.0 | 46.6 | 56.6 | 82.3 |
| 1-35 | WT | Water | 7.0 | 52.2 | 59.2 | 88.2 |
| 2-2 | WT | Water | 19.7 | 14.0 | 33.7 | 41.6 |
| 2-6 | WT | Water | 3.7 | 22.3 | 25.9 | 85.8 |
| 2-13 | WT | Water | 3.7 | 3.6 | 7.3 | 49.2 |
| 2-17 | WT | Water | 10.0 | 22.7 | 32.7 | 69.6 |
| 2-20 | WT | Water | 4.6 | 19.1 | 23.6 | 80.6 |
| 2-24 | WT | Water | 2.8 | 32.5 | 35.3 | 92.2 |
| 2-26 | WT | Water | 5.2 | 14.4 | 19.6 | 73.7 |
| 2-27 | WT | Water | 1.7 | 8.2 | 10.0 | 82.5 |
| 2-31 | WT | Water | 13.9 | 54.0 | 67.9 | 79.6 |
| 2-35 | WT | Water | 4.5 | 20.6 | 25.1 | 81.9 |
| | Mean | | 7.3 | 26.7 | 34.0 | 76.6 |
| | SEM | | 1.1 | 3.6 | 4.1 | 3.0 |

TABLE 4b

Discrimination of non-social odors by WT mice receiving rasagiline

| Mice (n = 18) | Genotype | Treatment | Time Sniffing F | Time Sniffing N | Total time sniffing | % time sniffing N |
|---|---|---|---|---|---|---|
| 1-1 | WT | Rasagiline | 2.6 | 25.4 | 28.0 | 90.6 |
| 1-5 | WT | Rasagiline | 3.1 | 11.1 | 14.2 | 78.1 |
| 1-17 | WT | Rasagiline | 34.2 | 24.2 | 58.4 | 41.5 |
| 1-18 | WT | Rasagiline | 6.2 | 37.4 | 43.6 | 85.8 |
| 1-23 | WT | Rasagiline | 3.6 | 59.6 | 63.2 | 94.3 |
| 1-29 | WT | Rasagiline | 28.9 | 52.1 | 81.0 | 64.3 |
| 1-33 | WT | Rasagiline | 3.8 | 4.3 | 8.1 | 53.0 |
| 1-36 | WT | Rasagiline | 27.1 | 44.5 | 71.6 | 62.2 |
| 1-37 | WT | Rasagiline | 18.4 | 31.3 | 49.7 | 63.0 |
| 2-1 | WT | Rasagiline | 14.1 | 24.8 | 39.0 | 63.7 |
| 2-5 | WT | Rasagiline | 3.3 | 19.4 | 22.8 | 85.3 |
| 2-9 | WT | Rasagiline | 1.2 | 6.6 | 7.8 | 85.2 |
| 2-12 | WT | Rasagiline | 13.8 | 10.4 | 24.2 | 43.0 |
| 2-14 | WT | Rasagiline | 6.2 | 30.6 | 36.8 | 83.3 |
| 2-18 | WT | Rasagiline | 15.9 | 33.0 | 48.9 | 67.4 |
| 2-23 | WT | Rasagiline | 11.9 | 40.4 | 52.3 | 77.3 |
| 2-33 | WT | Rasagiline | 0.3 | 65.6 | 65.9 | 99.6 |
| 2-38 | WT | Rasagiline | 19.1 | 29.8 | 48.9 | 61.0 |
| | Mean | | 11.9 | 30.6 | 42.5 | 72.1 |
| | SEM | | 2.4 | 4.1 | 5.1 | 4.0 |

TABLE 4c

Discrimination of non-social odors by untreated α-syn mutants

| Mice (n = 19) | Genotype | Treatment | Time Sniffing F | Time Sniffing N | Total time sniffing | % time sniffing N |
|---|---|---|---|---|---|---|
| 1-3 | Mutant | Water | 2.0 | 1.7 | 3.7 | 46.2 |
| 1-7 | Mutant | Water | 9.4 | 14.3 | 23.7 | 60.3 |
| 1-11 | Mutant | Water | 5.9 | 6.7 | 12.6 | 53.2 |
| 1-12 | Mutant | Water | 2.4 | 2.4 | 4.8 | 49.7 |
| 1-13 | Mutant | Water | 9.1 | 5.2 | 14.3 | 36.3 |
| 1-26 | Mutant | Water | 6.6 | 6.6 | 13.2 | 49.9 |
| 1-27 | Mutant | Water | 6.0 | 5.3 | 11.3 | 46.8 |
| 1-39 | Mutant | Water | 4.0 | 3.0 | 7.0 | 42.5 |
| 1-40 | Mutant | Water | 4.7 | 5.9 | 10.6 | 55.8 |
| 2-3 | Mutant | Water | 4.6 | 2.6 | 7.1 | 35.9 |
| 2-7 | Mutant | Water | 5.1 | 4.0 | 9.1 | 44.2 |
| 2-10 | Mutant | Water | 5.9 | 2.6 | 8.4 | 30.5 |
| 2-11 | Mutant | Water | 2.8 | 2.4 | 5.2 | 46.2 |
| 2-16 | Mutant | Water | 5.6 | 1.8 | 7.4 | 24.2 |
| 2-19 | Mutant | Water | 2.4 | 6.9 | 9.3 | 73.8 |
| 2-22 | Mutant | Water | 5.8 | 4.0 | 9.7 | 40.7 |
| 2-29 | Mutant | Water | 1.9 | 3.1 | 5.0 | 61.6 |
| 2-32 | Mutant | Water | 4.7 | 5.7 | 10.4 | 54.8 |
| 2-36 | Mutant | Water | 3.7 | 2.1 | 5.9 | 36.3 |
| | Mean | | 4.9 | 4.5 | 9.4 | 46.8 |
| | SEM | | 0.5 | 0.7 | 1.1 | 2.7 |

TABLE 4d

Discrimination of non-social odors by α-syn mutants receiving rasagiline

| Mice (n = 20) | Genotype | Treatment | Time Sniffing F | Time Sniffing N | Total time sniffing | % time sniffing N |
|---|---|---|---|---|---|---|
| 1-4 | Mutant | Rasagiline | 3.2 | 6.6 | 9.8 | 67.4 |
| 1-8 | Mutant | Rasagiline | 6.0 | 22.2 | 28.1 | 78.8 |
| 1-9 | Mutant | Rasagiline | 2.1 | 5.1 | 7.2 | 71.1 |
| 1-10 | Mutant | Rasagiline | 2.7 | 13.3 | 16.0 | 83.1 |
| 1-14 | Mutant | Rasagiline | 5.3 | 5.8 | 11.1 | 52.3 |
| 1-15 | Mutant | Rasagiline | 1.6 | 2.3 | 3.9 | 59.1 |
| 1-21 | Mutant | Rasagiline | 2.3 | 11.2 | 13.5 | 33.0 |
| 1-25 | Mutant | Rasagiline | 4.5 | 7.8 | 12.3 | 63.6 |
| 1-30 | Mutant | Rasagiline | 1.8 | 3.4 | 5.2 | 65.1 |
| 1-32 | Mutant | Rasagiline | 13.7 | 70.0 | 83.7 | 83.6 |
| 1-38 | Mutant | Rasagiline | 2.1 | 8.2 | 10.3 | 79.4 |
| 2-4 | Mutant | Rasagiline | 4.9 | 9.4 | 14.4 | 65.7 |
| 2-8 | Mutant | Rasagiline | 4.9 | 4.2 | 9.1 | 46.3 |
| 2-15 | Mutant | Rasagiline | 3.0 | 16.6 | 19.6 | 84.6 |
| 2-21 | Mutant | Rasagiline | 2.8 | 4.4 | 7.1 | 61.3 |
| 2-25 | Mutant | Rasagiline | 2.7 | 6.6 | 9.3 | 71.4 |
| 2-28 | Mutant | Rasagiline | 0.7 | 9.2 | 9.9 | 92.7 |
| 2-30 | Mutant | Rasagiline | 4.4 | 5.5 | 9.9 | 55.6 |
| 2-34 | Mutant | Rasagiline | 1.8 | 3.6 | 5.3 | 67.0 |
| 2-37 | Mutant | Rasagiline | 3.0 | 8.4 | 11.4 | 73.5 |
| | Mean | | 3.7 | 11.2 | 14.8 | 70.2 |
| | SEM | | 0.6 | 3.3 | 3.8 | 2.7 |

Discussion:

The results above demonstrate that rasagiline improves discrimination of two close non-social odors in α-syn mutant mice (FIG. 4B). The data in FIG. 4B were analyzed by 2-way ANOVA with Effect of the genotype $p<0.001$; Effect of the treatment $p<0.01$; Interaction genotype*treatment $p<0.001$; and Bonferroni post-hoc, ***$p<0.001$. FIG. 4B shows that mutants are impaired to discriminate 2 close non social odors and rasagiline improves the discrimination of 2 close non social odors.

EXAMPLE 5

Odor Preference Test

This experiment was a control test to determine if mice or the rasagiline treatment could interfere on the odor preference between lime and lemon. The time periods that mice spent sniffing lemon and lime were compared. The testing parameters were percentage of time of sniffing lemon out of total time of sniffing and percentage of time of sniffing lime out of total time of sniffing.

Results:

The results are summarized in tables 5a-5d. The analysis was performed by Kruskal-Wallis test to compare % time of sniffing between mouse groups, and a t-test to compare for each group the % of sniffing time of lime and lemon.

TABLE 5a

Odor preference of WT untreated mice

| Treatment Group | | | Time of sniffing (s) | | | % Time sniffing | |
|---|---|---|---|---|---|---|---|
| Mice (n = 21) | Genotype | Treatment | Lemon | Lime | Total | Lemon | Lime |
| 1-2 | WT | Water | 8.5 | 17.3 | 25.8 | 33.0 | 67.0 |
| 1-6 | WT | Water | 39.9 | 38.5 | 78.4 | 50.9 | 49.1 |
| 1-16 | WT | Water | 45.3 | 40.0 | 85.3 | 53.1 | 46.9 |
| 1-19 | WT | Water | 45.4 | 54.5 | 99.9 | 45.4 | 54.6 |
| 1-20 | WT | Water | 21.2 | 21.6 | 42.8 | 49.5 | 50.5 |
| 1-22 | WT | Water | 13.1 | 11.1 | 24.2 | 54.1 | 45.9 |
| 1-24 | WT | Water | 16.6 | 9.7 | 26.3 | 63.2 | 36.8 |
| 1-28 | WT | Water | 100.7 | 89.0 | 189.7 | 53.1 | 46.9 |
| 1-31 | WT | Water | 15.6 | 55.0 | 70.6 | 22.1 | 77.9 |
| 1-34 | WT | Water | 6.8 | 8.4 | 15.2 | 44.7 | 55.3 |
| 1-35 | WT | Water | 42.9 | 32.0 | 74.9 | 57.3 | 42.7 |
| 2-2 | WT | Water | 4.1 | 4.4 | 8.4 | 48.3 | 51.7 |
| 2-6 | WT | Water | 11.8 | 15.7 | 27.5 | 43.0 | 57.0 |
| 2-13 | WT | Water | 4.7 | 3.2 | 7.9 | 59.5 | 40.5 |
| 2-17 | WT | Water | 20.4 | 18.6 | 39.0 | 52.3 | 47.7 |
| 2-20 | WT | Water | 11.7 | 8.0 | 19.7 | 59.5 | 40.5 |
| 2-24 | WT | Water | 10.0 | 7.3 | 17.3 | 58.1 | 41.9 |
| 2-26 | WT | Water | 10.1 | 13.1 | 23.2 | 43.4 | 56.6 |
| 2-27 | WT | Water | 7.5 | 11.1 | 18.5 | 40.3 | 59.7 |
| 2-31 | WT | Water | 25.7 | 26.8 | 52.5 | 49.0 | 51.0 |
| 2-35 | WT | Water | 34.2 | 29.3 | 63.5 | 53.8 | 46.2 |
| | Mean | | 23.6 | 24.5 | 48.1 | 49.2 | 50.8 |
| | SEM | | 4.9 | 4.7 | 9.3 | 2.1 | 2.1 |

TABLE 5b

Odor preference of WT mice receiving rasagiline

| Treatment Group | | | Time of sniffing (s) | | | % Time sniffing | |
|---|---|---|---|---|---|---|---|
| Mice (n = 18) | Genotype | Treatment | Lemon | Lime | Total | Lemon | Lime |
| 1-1 | WT | Rasagiline | 23.2 | 14.4 | 37.6 | 61.7 | 38.3 |
| 1-5 | WT | Rasagiline | 10.3 | 6.9 | 17.2 | 59.9 | 40.1 |
| 1-17 | WT | Rasagiline | 12.5 | 14.2 | 26.7 | 47.0 | 53.0 |
| 1-18 | WT | Rasagiline | 106.9 | 33.5 | 140.4 | 76.1 | 23.9 |
| 1-23 | WT | Rasagiline | 46.8 | 80.7 | 127.5 | 36.7 | 63.3 |
| 1-29 | WT | Rasagiline | 31.9 | 15.1 | 47.0 | 67.9 | 32.1 |
| 1-33 | WT | Rasagiline | 3.6 | 4.3 | 7.9 | 45.7 | 54.3 |
| 1-36 | WT | Rasagiline | 54.9 | 96.8 | 151.7 | 36.2 | 63.8 |
| 1-37 | WT | Rasagiline | 20.6 | 13.5 | 34.1 | 60.4 | 39.6 |
| 2-1 | WT | Rasagiline | 32.1 | 10.3 | 42.4 | 75.8 | 24.2 |
| 2-5 | WT | Rasagiline | 3.9 | 7.5 | 11.4 | 33.9 | 66.1 |
| 2-9 | WT | Rasagiline | 6.0 | 6.5 | 12.4 | 47.9 | 52.1 |
| 2-12 | WT | Rasagiline | 6.5 | 8.7 | 15.2 | 42.7 | 57.3 |
| 2-14 | WT | Rasagiline | 32.2 | 37.7 | 70.0 | 46.1 | 53.9 |
| 2-18 | WT | Rasagiline | 20.1 | 13.5 | 33.6 | 59.9 | 40.1 |
| 2-23 | WT | Rasagiline | 21.8 | 15.1 | 37.0 | 59.1 | 40.9 |
| 2-33 | WT | Rasagiline | 14.2 | 10.5 | 24.7 | 57.5 | 42.5 |
| 2-38 | WT | Rasagiline | 18.0 | 30.4 | 48.4 | 37.2 | 62.8 |
| | Mean | | 25.9 | 23.3 | 49.2 | 52.9 | 47.1 |
| | SEM | | 5.8 | 6.1 | 10.5 | 3.1 | 3.1 |

TABLE 5c

Odor preference of untreated α-syn mutants

| Treatment Group | | | Time of sniffing (s) | | | % Time sniffing | |
|---|---|---|---|---|---|---|---|
| Mice (n = 19) | Genotype | Treatment | Lemon | Lime | Total | Lemon | Lime |
| 1-3 | Mutant | Water | 1.8 | 2.1 | 3.9 | 46.5 | 53.5 |
| 1-7 | Mutant | Water | 3.2 | 4.1 | 7.3 | 43.5 | 56.5 |
| 1-11 | Mutant | Water | 4.0 | 1.6 | 5.6 | 71.6 | 28.4 |
| 1-12 | Mutant | Water | 2.9 | 3.3 | 6.2 | 47.1 | 52.9 |
| 1-13 | Mutant | Water | 4.9 | 5.4 | 10.3 | 47.2 | 52.8 |
| 1-26 | Mutant | Water | 6.9 | 7.4 | 14.3 | 48.1 | 51.9 |
| 1-27 | Mutant | Water | 6.1 | 6.2 | 12.3 | 49.8 | 50.2 |
| 1-39 | Mutant | Water | 10.7 | 11.1 | 21.8 | 49.0 | 51.0 |
| 1-40 | Mutant | Water | 2.2 | 1.6 | 3.8 | 56.9 | 43.1 |
| 2-3 | Mutant | Water | 2.8 | 3.6 | 6.4 | 44.4 | 55.6 |
| 2-7 | Mutant | Water | 4.0 | 2.7 | 6.7 | 60.3 | 39.7 |
| 2-10 | Mutant | Water | 2.5 | 2.6 | 5.2 | 49.0 | 51.0 |
| 2-11 | Mutant | Water | 4.2 | 5.3 | 9.6 | 44.3 | 55.7 |
| 2-16 | Mutant | Water | 5.0 | 5.6 | 10.7 | 47.2 | 52.8 |
| 2-19 | Mutant | Water | 4.3 | 6.3 | 10.6 | 40.9 | 59.1 |
| 2-22 | Mutant | Water | 2.6 | 2.6 | 5.2 | 49.8 | 50.2 |
| 2-29 | Mutant | Water | 7.9 | 8.4 | 16.2 | 48.6 | 51.4 |
| 2-32 | Mutant | Water | 8.4 | 7.5 | 15.9 | 52.9 | 47.1 |
| 2-36 | Mutant | Water | 5.5 | 6.2 | 11.7 | 47.2 | 52.8 |
| | Mean | | 4.7 | 4.9 | 9.7 | 49.7 | 50.3 |
| | SEM | | 0.5 | 0.6 | 1.1 | 1.6 | 1.6 |

TABLE 5d

Odor preference of α-syn mutants receiving rasagiline

| Treatment Group | | | Time of sniffing (s) | | | % Time sniffing | |
|---|---|---|---|---|---|---|---|
| Mice (n = 19) | Genotype | Treatment | Lemon | Lime | Total | Lemon | Lime |
| 1-4 | Mutant | Rasagiline | 6.3 | 3.9 | 10.2 | 61.8 | 38.2 |
| 1-8 | Mutant | Rasagiline | 6.4 | 8.7 | 15.1 | 42.4 | 57.6 |
| 1-9 | Mutant | Rasagiline | 4.7 | 3.7 | 8.4 | 55.9 | 44.1 |
| 1-10 | Mutant | Rasagiline | 2.5 | 4.9 | 7.4 | 33.5 | 66.5 |
| 1-14 | Mutant | Rasagiline | 7.9 | 4.5 | 12.4 | 63.7 | 36.3 |
| 1-15 | Mutant | Rasagiline | 2.6 | 4.6 | 7.2 | 36.2 | 63.8 |
| 1-21 | Mutant | Rasagiline | 6.5 | 7.5 | 14.0 | 46.5 | 53.5 |
| 1-25 | Mutant | Rasagiline | 13.0 | 3.4 | 16.4 | 79.3 | 20.7 |
| 1-30 | Mutant | Rasagiline | 5.7 | 6.0 | 11.7 | 48.5 | 51.5 |
| 1-32 | Mutant | Rasagiline | 10.0 | 63.0 | 73.0 | 13.7 | 86.3 |
| 1-38 | Mutant | Rasagiline | 6.2 | 6.9 | 13.1 | 47.3 | 52.7 |
| 2-4 | Mutant | Rasagiline | 6.8 | 4.2 | 11.0 | 62.1 | 37.9 |
| 2-8 | Mutant | Rasagiline | 4.0 | 5.6 | 9.6 | 41.3 | 58.7 |
| 2-15 | Mutant | Rasagiline | 7.8 | 7.0 | 14.9 | 52.7 | 47.3 |
| 2-21 | Mutant | Rasagiline | 5.4 | 8.4 | 13.9 | 39.2 | 60.8 |
| 2-25 | Mutant | Rasagiline | 7.2 | 7.6 | 14.8 | 48.5 | 51.5 |
| 2-28 | Mutant | Rasagiline | 6.9 | 7.3 | 14.2 | 48.6 | 51.4 |
| 2-30 | Mutant | Rasagiline | 2.9 | 4.9 | 7.8 | 37.0 | 63.0 |
| 2-34 | Mutant | Rasagiline | 5.9 | 8.3 | 14.2 | 41.3 | 58.7 |
| 2-37 | Mutant | Rasagiline | 4.2 | 4.4 | 8.6 | 48.8 | 51.2 |
| | Mean | | 6.1 | 8.7 | 14.9 | 47.4 | 52.6 |
| | SEM | | 0.6 | 2.9 | 3.1 | 3.1 | 3.1 |

Figure 5:
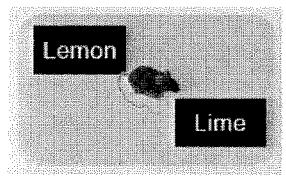
FIG. 5: Odor preference test in WT and mutant mice untreated or treated with rasagiline
Figure 5:
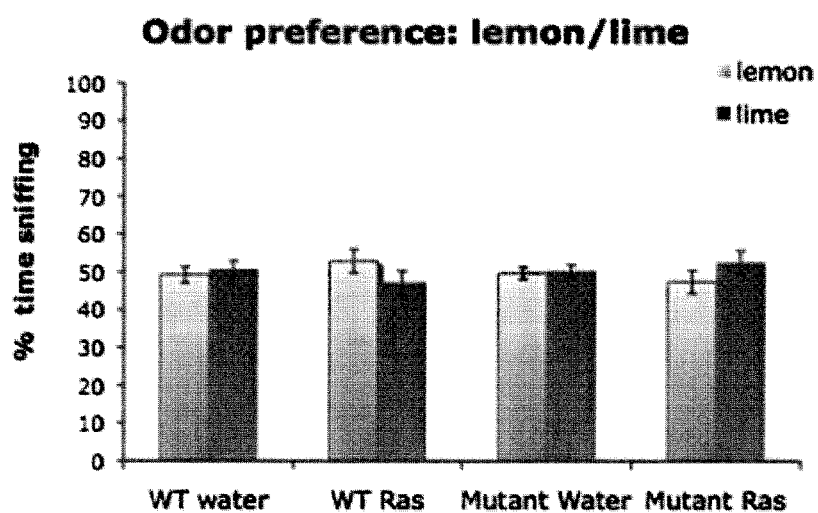

Discussion:

The results above demonstrate that there was no difference of odor preference between lemon and lime. For each odor, there was no difference in percentage of time sniffing between the groups (FIG. 5B). The data in FIG. 5B were analyzed for group comparison with Kruskal Wallis p>0.05 and lemon/lime comparison for each group with t-test (p>0.05). FIG. 5B shows that for each group: no difference of odor preference between lemon/lime and for each odor: no difference of % time sniffing between groups.

EXAMPLE 6

Novel Object Exploration Test

This experiment was a control test to determine if rasagiline has an effect on the level of the exploration of a novel object. The testing parameters were percentage of time exploring the novel object out of total time of the trial.

Results:

The results are summarized in tables 6a-6d. The analysis was performed by Kruskal-Wallis and Mann-Whitney post-hoc.

TABLE 6a

Novel object exploration of WT untreated mice

| Mice (n = 10) | Genotype | Treatment | Time of exploration (s) | % Time exploring novel object |
|---|---|---|---|---|
| 2 | WT | Water | 88.0 | 29.3 |
| 6 | WT | Water | 109.6 | 36.5 |
| 16 | WT | Water | 111.8 | 37.3 |
| 19 | WT | Water | 110.5 | 36.8 |
| 20 | WT | Water | 96.7 | 32.2 |
| 22 | WT | Water | 114.8 | 38.3 |
| 24 | WT | Water | 108.7 | 36.2 |
| 28 | WT | Water | 91.1 | 30.4 |
| 31 | WT | Water | 116.1 | 38.7 |
| 35 | WT | Water | 112.4 | 37.5 |
| Mean | | | 106.0 | 35.3 |
| SEM | | | 3.2 | 1.1 |

TABLE 6b

Novel object exploration of WT mice receiving rasagiline

| Mice (n = 9) | Genotype | Treatment | Time of exploration (s) | % Time exploring novel object |
|---|---|---|---|---|
| 1 | WT | Rasagiline | 98.0 | 32.7 |
| 5 | WT | Rasagiline | 98.4 | 32.8 |
| 17 | WT | Rasagiline | 105.6 | 35.2 |
| 18 | WT | Rasagilins | 115.1 | 38.4 |
| 23 | WT | Rasagilina | 100.0 | 33.3 |
| 29 | WT | Rasagiline | 113.4 | 37.8 |
| 33 | WT | Rasagiline | 99.8 | 33.3 |
| 36 | WT | Rasagiline | 110.5 | 36.8 |
| 37 | WT | Rasagiline | 109.1 | 36.4 |
| Mean | | | 105.5 | 35.2 |
| SEM | | | 2.2 | 0.7 |

TABLE 6c

Novel object exploration of untreated α-syn mutants

| Mice (n = 9) | Genotype | Treatment | Time of exploration (s) | % Time exploring novel object |
|---|---|---|---|---|
| 3 | Mutant | Watar | 20.6 | 6.9 |
| 7 | Mutant | Water | 91.6 | 30.5 |
| 11 | Mutant | Water | 44.0 | 14.7 |
| 12 | Mutant | Water | 61.9 | 20.6 |
| 13 | Mutant | Water | 106.0 | 35.3 |
| 26 | Mutant | Water | 102.8 | 34.3 |
| 27 | Mutant | Water | 55.4 | 18.5 |
| 39 | Mutant | Water | 116.0 | 38.7 |
| 40 | Mutant | Water | 108.1 | 36.0 |
| Mean | | | 78.5 | 26.2 |
| SEM | | | 11.3 | 3.8 |

TABLE 6d

Novel object exploration of α-syn mutants receiving rasagiline

| Mice (n = 11) | Genotype | Treatment | Time of exploration (s) | % Time exploring novel object |
|---|---|---|---|---|
| 4 | Mutant | Rasagiline | 60.6 | 20.2 |
| 8 | Mutant | Rasagiline | 103.5 | 34.5 |
| 9 | Mutant | Rasagiline | 67.6 | 22.5 |
| 10 | Mutant | Rasagiline | 43.5 | 14.5 |
| 14 | Mutant | Rasagiline | 73.6 | 24.5 |
| 15 | Mutant | Rasagiline | 69.4 | 23.1 |
| 21 | Mutant | Rasagiline | 106.1 | 35.4 |
| 25 | Mutant | Rasagiline | 85.8 | 28.6 |
| 30 | Mutant | Rasagiline | 53.1 | 17.7 |
| 32 | Mutant | Rasagiline | 108.2 | 36.1 |
| 38 | Mutant | Rasagiline | 101.4 | 33.8 |
| Mean | | | 79.3 | 26.4 |
| SEM | | | 6.9 | 2.3 |

Figure 6:
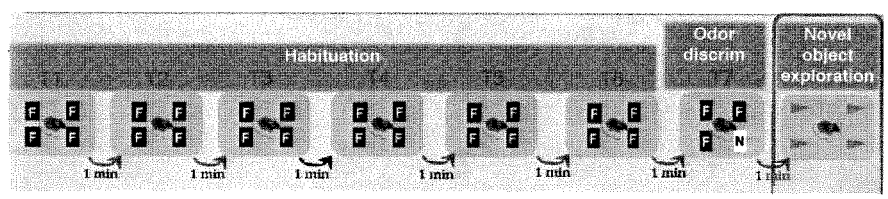
FIG. 6: Effect of rasagiline on object exploration of WT and mutant mice untreated or treated with rasagiline.
Figure 6:
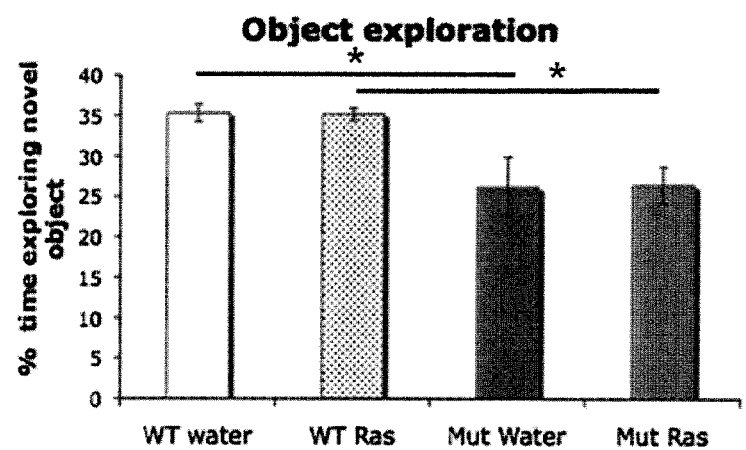

Discussion:

The results above demonstrate that rasagiline has no effect on novel object exploration of the WT and mutant animals (FIG. 6B). The data in FIG. 6B were analyzed with Kruskal-Wallis ($p<0.05$) and Mann Whitney post-hoc test (*$p<0.05$). FIG. 6B shows that mutants are impaired in exploring a novel object compared to WT and rasagiline exhibits no effect on exploring a novel object.

EXAMPLE 7

Discrimination of a Novel Object/Odor

Figure 7:
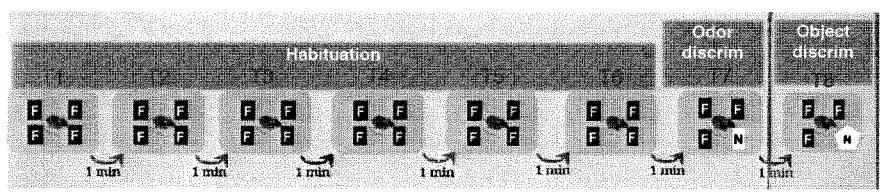
FIG. 7: Effect of rasagiline on object/odor discrimination of WT and mutant mice untreated or treated with rasagiline.
Figure 7:
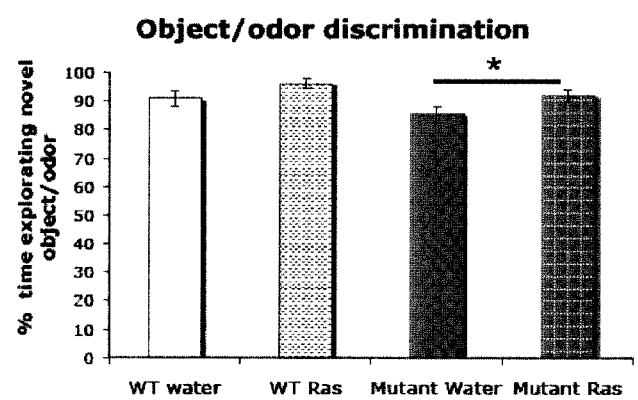

This experiment was a control test to determine the object/odor discrimination ability of mutant mice and animal treated with rasagiline. The objective was to determine whether the odor discrimination deficit was specific to the olfactory function (FIG. 7A).

The testing parameters was percentage of time exploring the novel object/odor out of total time of exploration.

Results:

The results are summarized in tables 7a-7d. The analysis was performed by 2-way ANOVA and Bonferroni post-hoc.

TABLE 7a

Novel object/odor exploration of WT untreated mice

| Mice (n = 10) | Genotype | Treatment | Familiar object | Novel object | Total | % Time exploring novel object |
|---|---|---|---|---|---|---|
| 2 | WT | Water | 2.2 | 72.0 | 74.2 | 97.0 |
| 6 | WT | Water | 3.7 | 81.2 | 84.8 | 95.7 |
| 13 | WT | Water | 2.5 | 14.7 | 17.2 | 55.7 |
| 17 | WT | Water | 1.9 | 104.6 | 106.5 | 98.2 |
| 20 | WT | Water | 3.9 | 18.1 | 22.0 | 82.4 |
| 24 | WT | Water | 1.4 | 92.5 | 93.9 | 98.5 |
| 26 | WT | Water | 6.9 | 21.6 | 28.5 | 75.8 |
| 27 | WT | Water | 4.9 | 48.7 | 53.6 | 90.9 |
| 31 | WT | Water | 7.2 | 48.7 | 55.9 | 87.1 |
| 35 | WT | Water | 1.5 | 66.8 | 68.3 | 97.8 |
| Mean | | | 3.6 | 56.9 | 60.5 | 90.9 |
| SEM | | | 0.7 | 10.1 | 9.7 | 2.5 |

TABLE 7b

Novel object/odor exploration of WT mice receiving rasagiline

| Mice (n = 9) | Treatment Group | | Time of Exploration (s) | | | % Time |
|---|---|---|---|---|---|---|
| | Genotype | Treatment | Familiar object | Novel object | Total | exploring novel object |
| 1 | WT | Rasagiline | 1.1 | 108.3 | 109.4 | 99.0 |
| 5 | WT | Rasagiline | 2.0 | 78.6 | 80.6 | 97.5 |
| 9 | WT | Rasagiline | 2.8 | 70.9 | 73.7 | 96.3 |
| 12 | WT | Rasagiline | 0.7 | 92.6 | 93.3 | 99.2 |
| 14 | WT | Rasagiline | 11.6 | 70.2 | 81.8 | 85.8 |
| 18 | WT | Rasagiline | 0.4 | 103.9 | 104.3 | 99.7 |
| 23 | WT | Rasagiline | 6.6 | 65.9 | 72.6 | 90.9 |
| 33 | WT | Rasagiline | 1.6 | 92.9 | 94.5 | 98.4 |
| 38 | WT | Rasagiline | 0.4 | 81.6 | 82.0 | 99.5 |
| | Mean | | 3.0 | 85.0 | 88.0 | 96.2 |
| | SEM | | 1.3 | 5.1 | 4.4 | 1.6 |

TABLE 7c

Novel object/odor exploration of untreated α-syn mutants

| Mice (n = 10) | Treatment Group | | Time of Exploration (s) | | | % Time |
|---|---|---|---|---|---|---|
| | Genotype | Treatment | Familiar object | Novel object | Total | exploring novel object |
| 3 | Mutant | Water | 3.3 | 13.0 | 16.3 | 79.7 |
| 7 | Mutant | Water | 2.8 | 34.2 | 37.0 | 92.4 |
| 10 | Mutant | Water | 2.8 | 36.6 | 39.4 | 92.9 |
| 11 | Mutant | Water | 2.7 | 8.2 | 11.0 | 75.3 |
| 16 | Mutant | Water | 2.3 | 7.3 | 9.7 | 75.8 |
| 19 | Mutant | Water | 1.0 | 55.7 | 56.6 | 98.3 |
| 22 | Mutant | Water | 4.4 | 18.5 | 22.9 | 81.0 |
| 29 | Mutant | Water | 1.9 | 31.1 | 33.0 | 94.2 |
| 32 | Mutant | Water | 2.0 | 14.2 | 16.2 | 87.4 |
| 36 | Mutant | Water | 4.7 | 16.9 | 21.6 | 78.2 |
| | Mean | | 2.8 | 23.6 | 26.4 | 85.5 |
| | SEM | | 0.4 | 4.9 | 4.7 | 2.7 |

TABLE 7d

Novel object/odor exploration of α-syn mutants receiving rasagiline

| Mice (n = 9) | Treatment Group | | Time of Exploration (s) | | | % Time |
|---|---|---|---|---|---|---|
| | Genotype | Treatment | Familiar object | Novel object | Total | exploring novel object |
| 4 | Mutant | Rasagiline | 2.8 | 41.7 | 44.5 | 93.7 |
| 8 | Mutant | Rasagiline | 3.0 | 25.8 | 28.8 | 89.7 |
| 15 | Mutant | Rasagiline | 12.2 | 75.2 | 87.5 | 86.0 |
| 21 | Mutant | Rasagiline | 2.7 | 58.4 | 61.0 | 95.6 |
| 25 | Mutant | Rasagiline | 0.5 | 57.2 | 57.8 | 99.1 |
| 28 | Mutant | Rasagiline | 2.8 | 67.0 | 69.8 | 96.0 |
| 30 | Mutant | Rasagiline | 1.8 | 42.7 | 44.5 | 95.9 |
| 34 | Mutant | Rasagiline | 4.4 | 60.3 | 64.7 | 93.2 |
| 37 | Mutant | Rasagiline | 2.5 | 10.2 | 12.7 | 80.7 |
| | Mean | | 3.6 | 48.7 | 52.4 | 92.2 |
| | SEM | | 1.1 | 6.9 | 7.5 | 1.9 |

Discussion:

The results above demonstrated that mutant mice exhibit similar object/odor discrimination ability compared to control meaning that the odor discrimination deficit seems to be specific to olfactory function. The data in FIG. 7B were analyzed by 2-way ANOVA with effect of the genotype $p<0.05$; effect of the treatment $p<0.05$; no interaction genotype*treatment; and Bonferroni post-hoc, $*p<0.05$. The data in FIG. 7B suggest that discrimination ability of the mutants certainly because of its effect on odor discrimination improvement. FIG. 7B shows that mutants are able to discriminate the novel object/odor and that rasagiline treatment improves the discrimination ability of the mutants to substantially WT levels.

EXAMPLE 8

Study of the Effect of Rasagiline on Olfactory Dysfunction

This experiment is designed to study the effect of rasagiline on olfactory dysfunction following the procedures described in two transgenic mouse models for the study of olfactory loss. (Lane et al., "Development of transgenic mouse models for the study of human olfactory dysfunction", Am J. Rhinol., 2005, May-June; 19(3):229-35.)

Each model shows that rasagiline is effective in treating the symptoms of olfactory dysfunction in the mice.

The study results also show that rasagiline is effective in reducing the rate of progression of olfactory dysfunction in the mice.

The study results also show that rasagiline is effective in reducing the functional decline in the mice.

REFERENCES

1. Grand Rounds Presentation, UTMB, Dept. of Otolaryngology, "Olfactory Dysfunction and Disorders", http://www.utmb.edu/otoref/grnds/Olfactory-2003-1126/Olfactory-2003-1126.htm.
2. Fleming S M, Tetreault N A, Mulligan C K, Hutson C B, Masliah E, Chesselet M F., "Olfactory deficits in mice overexpressing human wildtype alpha-synuclein", Eur J. Neurosci. 2008 July; 28(2):247-56.

What is claimed is:

1. A method of treating a symptom of olfactory dysfunction in a subject afflicted by olfactory dysfunction, the method comprising:
   a. identifying the subject as afflicted by olfactory dysfunction, and
   b. periodically administering to the subject so identified an amount of R(+)-N-propargyl-1-aminoindan or a pharmaceutically acceptable salt thereof, effective to treat the subject,
   wherein the subject is a non-Parkinson's disease subject.

2. A method of reducing the rate of progression of olfactory dysfunction in a non-Parkinson's disease subject afflicted by olfactory dysfunction, the method comprising periodically administering to the subject an amount of R(+)-N-propargyl-1-aminoindan or a pharmaceutically acceptable salt thereof effective to reduce the rate of progression of olfactory dysfunction in the non-Parkinson's disease subject.

3. A method of inhibiting loss of olfactory function in a non-Parkinson's disease subject, the method comprising periodically administering to the subject an amount of R(+)-N-propargyl-1-aminoindan or a pharmaceutically acceptable salt thereof effective to inhibit loss of olfactory function in the non-Parkinson's disease subject.

4. The method of claim 1, wherein the amount of R(+)-N-propargyl-1-aminoindan or of the pharmaceutically acceptable salt thereof is from 0.01 mg to 5 mg per day.

5. The method of claim 4, wherein the amount of R(+)-N-propargyl-1-aminoindan or of the pharmaceutically acceptable salt thereof is 0.5 mg per day.

6. The method of claim 4, wherein the amount of R(+)-N-propargyl-1-aminoindan or of the pharmaceutically acceptable salt thereof is 2 mg per day.

7. The method of claim 4, wherein the amount of R(+)-N-propargyl-1-aminoindan or of the pharmaceutically acceptable salt thereof is 1 mg per day.

8. The method of claim 1, wherein R(+)-N-propargyl-1-aminoindan is administered in the form of free base.

9. The method of claim 1, wherein the pharmaceutically acceptable salt of R(+)-N-propargyl-1-aminoindan is esylate, mesylate, sulphate, citrate or tartrate.

10. The method of claim 9, wherein the pharmaceutically acceptable salt is a mesylate salt.

11. The method of claim 9, wherein the pharmaceutically acceptable salt is a citrate salt.

12. The method of claim 1, wherein the olfactory dysfunction is selected from the group consisting of anosmia, partial anosmia, hyposmia, hyperosmia, dysosmia, phantosmia, and olfactory agnosia.

13. The method of claim 1, wherein the amount of R(+)-N-propargyl-1-aminoindan or a pharmaceutically acceptable salt thereof is formulated in oral, parenteral, rectal, or transdermal formulation.

* * * * *